United States Patent [19]

Edwards et al.

[11] Patent Number: 5,532,366
[45] Date of Patent: Jul. 2, 1996

[54] HETEROCYCLIC AMIDES

[75] Inventors: Philip D. Edwards, Kennett Square, Pa.; Peter Warner, Macclesfield, United Kingdom; Donald J. Wolanin, Orange, Conn.

[73] Assignee: Zeneca Limited, London, England

[21] Appl. No.: 375,201

[22] Filed: Jan. 19, 1995

Related U.S. Application Data

[63] Continuation of Ser. No. 86,780, Jul. 1, 1993, abandoned.

[30]    Foreign Application Priority Data

Jul. 2, 1992 [GB] United Kingdom ............ 9214053

[51] Int. Cl.$^6$ .................. A61K 31/505; C07D 471/04
[52] U.S. Cl. .................. 514/234.2; 544/117; 544/279; 514/257; 546/297
[58] Field of Search ................ 544/279, 117; 514/234.2, 257

[56]         References Cited

U.S. PATENT DOCUMENTS

| | | | |
|---|---|---|---|
| 4,808,618 | 2/1989 | Go et al. | 544/279 |
| 4,910,190 | 3/1990 | Bergeson et al. | 514/19 |
| 5,254,558 | 10/1993 | Bernstein | 544/296 |

FOREIGN PATENT DOCUMENTS

| | | |
|---|---|---|
| 0399688A1 | 11/1990 | European Pat. Off. . |
| 0509769A2 | 10/1992 | European Pat. Off. . |
| 0528633A1 | 2/1993 | European Pat. Off. . |

OTHER PUBLICATIONS

Zimmerman, "Elastin and Elastases" (CRC Press, 1989), pp. 109–123.
Janoff, Am. Rev. Resp. Dis. 121, 1025 (1980).
Trainor, *TIPS* 8, 303–307 (1987).
Zimmerman, Am. J. Physiol. 259, H390 (1990).
Kennedy, Eur. J. Resp. Dis 71, 472 (1987).
Sommerhoff, Eur. J. Pharm. 193, 153 (1991).
Bonney, J. Cellular Biochemistry 39, 47–53 (1989).
Abstract of Wewers, J. Clin. Inves. 82, 1260 (1988).
"Organic Chemistry, 4th Edition", Morrison & Boyd, 1980 p. 573.
"IUPAC Nomenclature of Organic Chemistry", Section A–F and H, (1979, Pergamon) pp. 305–307, 316.
J. W. Skiles, et al. "Inhibition of Human Leukocyte Elastase (HLE) by N–Substituted Peptidyl Trifluoromethyl Ketones" *J. Med. Chem.*, 1992, 35, 641–662.

*Primary Examiner*—Mark L. Berch
*Attorney, Agent, or Firm*—Liza D. Hohenschutz; Michael D. Alexander; Ruth H. Newtson

[57]         ABSTRACT

The present invention relates to certain novel amide derivatives which are pyrido[3,4-d]pyrimidin-7-ylacetamides which are inhibitors of human leukocyte elastase (HLE), also known as human neutrophil elastase (HNE), making them useful whenever such inhibition is desired, such as for research tools in pharmacological, diagnostic and related studies and in the treatment of diseases in mammals in which HLE is implicated. The invention also includes intermediates useful in the synthesis of these amide derivatives, processes for preparing the amide derivatives, pharmaceutical compositions containing such amide derivatives and methods for their use.

11 Claims, No Drawings

5,532,366

HETEROCYCLIC AMIDES

This is a continuation of application Ser. No. 08/086,780 filed on Jul. 1, 1993 abandoned.

The present invention relates to certain heterocyclic amides, in particular, certain pyrido[3,4-d]pyrimidin-7-ylacetamides, which are inhibitors of human leukocyte elastase (HLE), also known as human neutrophil elastase (HNE), making them useful whenever such inhibition is desired, such as for research tools in pharmacological, diagnostic and related studies and in the treatment of diseases in mammals in which HLE is implicated. For example, HLE has been implicated in the pathogenesis of acute respiratory distress syndrome (ARDS), rheumatoid arthritis, atherosclerosis, pulmonary emphysema, and other inflammatory disorders, including airway inflammatory diseases characterized by increased and abnormal airway secretion such as chronic bronchitis and cystic fibrosis. Also, HLE has been implicated in certain vascular diseases and related conditions (and their therapy) in which neutrophil participation is involved or implicated, for example, in hemorrhage associated with acute non-lymphocytic leukemia, as well as in reperfusion injury associated with, for example, myocardial ischaemia and related conditions associated with coronary artery disease such as angina and infarction, cerebrovascular ischaemia such as transient ischaemic attack and stroke, peripheral occlusive vascular disease such as intermittent claudication and critical limb ischaemia, venous insufficiency such as venous hypertension, varicose veins and venous ulceration, as well as impaired reperfusion states such as those associated with reconstructive vascular surgery, thrombolysis and angioplasty. The invention also includes intermediates useful in the synthesis of these heterocyclic amides, processes for preparing the heterocyclic amides, pharmaceutical compositions containing such heterocyclic amides and methods for their use.

In U.S. Pat. No. 4,910,190, of 20 Mar. 1990, assigned to ICI Americas Inc.(now Zeneca Inc.), there is disclosed a series of peptidoyl trifluoromethane derivatives which are HLE inhibitors. Disclosed herein is a series of substituted 2-(2,4,8-trioxo-1,2,3,4,7,8-hexahydropyrido[3,4-d]pyrimidin-7-yl)-N-(3,3,3-trifluoro-1-alkyl-2-oxopropyl)acetamides which unexpectedly possess inhibitory properties against HLE, which provides the basis for the present invention.

According to the invention there is provided a Compound of the invention which is a compound of formula I (formula set out, together with other formulae referred to by Roman numerals, following the Examples) wherein:

$R^0$ is (1–5C)alkyl;

$R^1$ is hydrogen, NReRf; or $R^1$ is (1–6C)alkyl, (3–6C)cycloalkyl, phenacyl, aryl, acetonyl or heteroaryl any of which may bear one or more substituents selected from a group consisting of hydroxy, (1–4C)alkyl, (1–4C)alkoxy, (1–4C)acyloxy, COORa, CONRbRc, COO(CH$_2$)$_2$NReRf, cyano, SO$_2$R$^5$, CONRdSO$_2$R$^5$, NReRf, NRgCOR$^6$, NRgCOOR$^6$, NRhCONRiRj, NRkSO$_2$R$^3$, SO$_2$NRlRm, SO$_2$NRnCOR$^4$, P(O)(ORa)$_2$, aryl and heteroaryl; and wherein an aryl or heteroaryl moiety of $R^1$ or a substituent thereof may bear one or more halogeno, nitro, (1–4C)alkyl, (1–4C)alkoxy or trifluoromethyl groups; wherein Ra–Rn are independently hydrogen, benzyl or (1–4C)alkyl; or, independently, a group NRbRc, NReRf, NRiRj or NRlRm is a cyclic radical selected from a group consisting of 1-pyrrolidinyl, piperidino, morpholino or 1-piperazinyl which may bear a (1–4C)alkyl or a halogeno substituent at the 4-position; or, independently, a group NReRf is a cyclic radical selected from a group consisting of 2-pyrrolidinon-1-yl, succinimido, oxazolidin-2-on-3-yl, 2-benzoxazolinon-3-yl, phthalimido and cis-hexahydrophthalimido; and $R^3$–$R^6$ are independently trifluoromethyl, (1–6C)alkyl, (3–6C)cycloalkyl, aryl or heteroaryl in which the aryl or heteroaryl may bear one or more substituents selected from a group consisting of (1–4C)alkyl, hydroxy, (1–4C)alkoxy, halogeno or trifluoromethyl;

$R^2$ is hydrogen, (1–6C)alkyl, (3–6C)cycloalkyl or a radical of formula B.Y— in which B is aryl or heteroaryl and may bear an aryl, or heteroaryl substituent and in which B or an aryl or heteroaryl substituent on B may independently bear one or more substituents selected from the group consisting of halogeno, nitro, (1–6C)alkyl, (3–6C)cycloalkyl, trifluoromethyl, cyano, hydroxy, (1–6C)alkoxy, lower acyloxy, SO$_2$Ro, COORq, CONRrRs; wherein Rq–Rs are independently hydrogen or (1–4C)alkyl;

Ro is (1–4C)alkyl; and

Y is a direct bond, methylene, ethylene, or trans-vinylene; and provided that no aliphatic carbon is bonded to more than one nitrogen or oxygen, except as part of a cyclic ketal or where the nitrogen bears a carbonyl group; or for a compound of formula I which is acidic or basic, a pharmaceutically acceptable salt thereof.

In this specification, the following definitions are used, unless otherwise described: Halogeno is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically referred to. Lower acyloxy refers to a radical containing one to about five carbon atoms. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms selected from the group consisting of oxygen, sulfur and nitrogen, as well as a radical of an ortho-fused bicyclic heterocycle of about eight to ten ring atoms derived therefrom, particularly a benz-derivative or one derived by fusing a propenylene, trimethylene or tetramethylene diradical thereto, as well as a stable N-oxide thereof.

It will be appreciated that, owing to the asymmetrically substituted carbon atom at the chiral center indicated by "*" in formula I, a compound of formula I may exist in, and be isolated in, optically active and racemic forms. If a compound of formula I contains an additional chiral element, such compound of formula I may exist in, and be isolated in, the form of a diastereomeric mixture or as a single diastereomer. It is to be understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer. When $R^0$ is isopropyl, a compound of formula I may be viewed as an alanyl trifluoromethane derivative. In general, a compound of formula I having the (S)-configuration at the chiral center indicated by "*", which corresponds to the L-alanyl configuration, is preferred. Accordingly, it may be preferred to use the compound of formula I in a form which is characterized as containing, for example, at least 95%, 98% or 99% enantiomeric excess (ee) of the (S)-form. However, owing to the interconvertability of the (S)-isomer and the (R)-isomer by the facile epimerization of the chiral center indicated by "*" in formula I, it may be preferred to utilize a compound of formula I as a mixture of the (S)- and (R)-isomers at the center indicated by "*" in formula I.

It is preferred that the radicals $R^0$, $R^1$, and $R^2$ not contain nor introduce an additional element of chirality into the molecule beyond the chiral center indicated by "*" in formula I.

As will be appreciated by those skilled in the art, a trifluoromethyl ketone of formula I can exist as a solvate, particularly a hydrate; and such a solvate of a compound of formula I is encompassed by the present invention.

A compound of formula I may exhibit polymorphism. The compound may form solvates in addition to a ketone solvate mentioned above. A compound may exist in more than one tautomeric form. It is to be understood, therefore, that the present invention encompasses any racemic or optically-active form, any polymorphic form, any tautomer or any solvate, or any mixture thereof, which form possesses inhibitory properties against HLE, it being well known in the art how to prepare optically active forms (for example, by resolution of the racemic form or by synthesis from optically-active starting materials) and how to determine the inhibitory properties against HLE by the standard tests described hereinafter.

Particular values are listed below for radicals, substituents and ranges are for illustration only and they do not exclude other defined values or other values within defined ranges for the radicals and substituents.

A particular group of compounds are those in which:

$R^1$ is hydrogen; or $R^1$ is (1–6C)alkyl, (3–6C)cycloalkyl, phenacyl, aryl or heteroaryl any of which may bear one or more substituents selected from a group consisting of hydroxy, (1–4C)alkyl, (1–4C)alkoxy, (1–4C)acyloxy, COORa, CONRbRc, COO(CH$_2$)$_2$NReRf, cyano, SO$_2$R$^5$, CONRdSO$_2$R$^5$, NReRf, NRgCOR$^6$, NRgCOOR$^6$, NRhCONRiRj, NRkSO$_2$R$^3$, SO$_2$NRlRm, SO$_2$NRnCOR$^4$, P(O)(ORa)$_2$, aryl and heteroaryl; and wherein an aryl or heteroaryl moiety of $R^1$ or a substituent thereof may bear one or more halogeno, nitro, (1–4C)alkyl, (1–4C)alkoxy or trifluoromethyl groups; and the other radicals are defined as above.

A particular value for $R^0$ is ethyl or isopropyl.

A particular value for (1–4C)alkyl is methyl, ethyl, propyl, isopropyl, butyl, isobutyl, or tert-butyl. A particular value of (1–6C)alkyl is methyl, ethyl, propyl, isopropyl, butyl, isobutyl, tert-butyl, pentyl, 3-methylbutyl, 1-ethylpropyl, hexyl or 4-methylpentyl. A particular value of (3–6C)cycloalkyl is cyclopropyl, cyclopentyl or cyclohexyl. A particular value for aryl is phenyl, indenyl, naphthyl, or 4-halophenyl. A particular value for heteroaryl is furyl, imidazolyl, tetrazolyl, pyridyl (or its N-oxide), thienyl, pyrimidinyl (or its N-oxide), indolyl or quinolinyl (or its N-oxide). A particular value for lower acyloxy is acetoxy. A particular value for (1–4C)alkoxy is methoxy, ethoxy, propoxy, isopropoxy or t-butoxy. A particular value for halogeno is bromo, chloro or fluoro.

A particular value for Ra, Rd, Rg, Rh, Rk and Rn independently is hydrogen, methyl or ethyl. A particular value for Rb, Rc, Re, Rf, Ri, Rj, Rl and Rm independently is methyl, ethyl, isopropyl or a particular value for the group NRbRc, NReRf, NRiRj or NRlRm is independently morpholino, 1-pyrolidinyl, piperidino or 1-piperazinyl. A particular value for $R^3$–$R^6$ independently is methyl, ethyl, isopropyl or phenyl.

A particular value for $R^1$ is 1-naphthylmethyl, 2-(1-naphthyl)ethyl, phenethyl, α,α-dimethylphenethyl, methyl, benzyloxycarbonylmethyl or 4-methoxybenzyl.

A particular value for $R^2$ is hydrogen or phenyl.

A more particular value for $R^0$ is isopropyl.

A more particular value for $R^1$ is 1-naphthylmethyl, 2-(1-naphthyl)ethyl, α,α-dimethylphenethyl or benzyloxycarbonylmethyl.

A more particular group of compounds of formula I is one in which $R^0$ has any of the values defined above, $R^1$ is 1-naphthylmethyl, 2-(1-naphthyl)ethyl, α,α-dimethylphenethyl or benzyloxycarbonylmethyl and $R^2$ is hydrogen.

Another more particular group of compounds of formula I is one in which $R^0$ has any of the values defined above, $R^1$ is 1-naphthylmethyl, 2-(1-naphthyl)ethyl, α,α-dimethylphenethyl or benzyloxycarbonylmethyl and $R^6$ is phenyl in which the phenyl may bear one or two halogeno, trifluoromethyl, methyl, hydroxy, methoxy, tert-butoxy, methoxycarbonyl or carboxy substituents; and, more particularly, $R^2$ is phenyl.

Specific compounds of formula I are described in the accompanying Examples.

Pharmaceutically acceptable salts of an acidic compound of formula I include alkalai metal salts (especially lithium, sodium and potassium), alkaline earth metal salts (especially calcium and magnesium), aluminum salts and ammonium salts, as well as salts made from appropriate organic bases such as triethylamine, morpholine, piperidine and triethanol amine. Pharmaceutically acceptable salts of a basic compound of formula I include acid-addition salts such as those made with a strong acid, for example hydrochloric, sulfuric or phosphoric acid, which acid provides a pharmaceutically acceptable anion.

A compound of formula I may be made by processes which include processes known in the chemical art for the production of structurally analogous heterocyclic and peptidic compounds. Such processes and intermediates for the manufacture of a compound of formula I as defined above are provided as further features of the invention and are illustrated by the following procedures in which the meanings of generic radicals are as defined above:

(A) Oxidizing a corresponding alcohol of formula II. A convenient method is the use of excess dimethyl sulfoxide and a water soluble carbodimide, with dichloroacetic acid as a catalyst, in an inert solvent such as toluene at about room temperature, for example as described in Example 1. Other methods which may be useful include the use of alkaline aqueous potassium permanganate solution; the use of oxalyl chloride, dimethyl sulfoxide and a tertiary amine; the use of acetic anhydride and dimethyl sulfoxide; the use of chromium trioxide pyridine complex in methylene chloride; and the use of a hypervalent iodine reagent, such as a periodinane, for example 1,1,1-triacetoxy-2,1-benzoxidol-3(3H)-one with trifluoroacetic acid in dichloromethane.

(B) For a compound of formula I which bears a hydroxy substituent on an aryl or heteroaryl group, cleaving the alkyl ether or acyloxy ester of a corresponding compound of formula I which bears a (1–4C)alkoxy or lower acyloxy substituent on an aryl or heteroaryl group. Convenient methods include, for example, the cleavage of a methoxy group using boron tribromide, the cleavage of a tert-butoxy group using trifluoroacetic acid, and the acidic or alkaline hydrolysis of an acyloxy group.

(C) For a compound of formula I which bears a group of formula COORa or COORg in which Ra or Rg is hydrogen (a carboxy group), decomposing the ester group of a corresponding ester made with a conveniently removed acid protecting group. The decomposition may be carried out using any one of the variety of procedures well known in organic chemistry, for example basic hydrolysis using lithium or sodium hydroxide (as in Example 3), or by hydrogenolysis of a benzyl ester.

(D) For a compound of formula I which contains an amino N-H residue, removal of the nitrogen protecting group of a corresponding compound bearing a conventional nitrogen protecting group by using a conventional method, for example, removal of a benzyloxycarbonyl group by hydrogenolysis, removal of a benzyloxycarbonyl or tert-butoxycarbonyl group by treatment with a strong acid, for example with trifluoromethanesulfonic acid in an inert solvent such as dichloromethane, or basic hydrolysis of a trifluoroacetyl group.

(E) For a compound of formula I which bears a heteroaryl N-oxide group, oxidation of a corresponding compound of formula I which bears a heteroaryl group using a conventional oxidant, such as for example peracetic acid or dioxirane in acetone.

(F) For a compound of formula I which bears a primary amino group, reduction of a corresponding compound bearing a nitro group using a conventional reducing method, such as for example, hydrogenation over a palladium catalyst, reduction with tin(II) chloride, or reduction with iron in acetic acid.

Whereafter, for any of the above procedures, when a pharmaceutically acceptable salt of an acidic or basic compound of formula I is required, it may be obtained by reacting the acidic or basic form of such a compound of formula I with a base or acid affording a physiologically acceptable counterion or by any other conventional procedure.

If not commercially available, the necessary starting materials for the above procedures may be made by procedures which are selected from standard techniques of heterocyclic chemistry and peptide chemistry, techniques which are analogous to the synthesis of known, structurally similar compounds, and techniques which are analogous to the above described procedures or the procedures described in the Examples. For uniformity and clarity, compounds herein are represented as the oxo tautomers, rather than the hydroxy tautomers.

As will be clear to one skilled in the art, a number of sequences is available for the preparation of the starting materials shown. For one such sequence, a key intermediate is a pyridone acid of formula IIIb, in which Rp is a suitable alcohol protecting group, such as for example methoxymethyl, 2-(trimethylsilyl)ethoxymethyl or, as described in Example 1, tert-butyldimethylsilyl, which may be prepared as shown in Scheme I (set out together with other Schemes, following the Examples). In the schemes, CBZ represents a benzyloxycarbonyl group, E represents an ethoxycarbonyl group and M represents a methoxycarbonyl group.

Following one of the sequences described in the examples, an amino alcohol of formula VI may be transformed into a corresponding glycine amide derivative of formula VII using procedures similar to those described in Examples 1.a.–1.c. for a compound in which $R^0$ is isopropyl. The compound of formula VIII, prepared by the condensation of ethyl pyruvate and dimethyl malonate, may be condensed with an amide of formula IX to provide a corresponding diene of formula X, for example as described in Example 1.k. for a compound in which $R^2$ is hydrogen. Alternatively, a salt of formula XI may be prepared from a non-enolizable amide of formula IX and subsequently condensed with the compound of formula VIII to provide a corresponding diene of formula X, for example as described in Example 16.a.–16.c. for a compound in which $R^2$ is phenyl.

Cyclization of a compound of formula VII with a compound of formula X, for example as described in Example 1.d., affords a corresponding diester of formula IIIa.

By following another sequence described in the examples, a pyridone of formula XII, which may be obtained form a corresponding compound of formula X, for example as described in Example 1.p.–1.q., may be alkylated with an iodide of formula XIII, prepared from a corresponding amino alcohol of formula VI for example as described in Example 1.1.–1.n., to provide a corresponding diestar of formula IIIa.

By selective decomposition of the ester at the 3-position of a pyridone of formula IIIa, for example using conditions similar to those described in Example 1.e., a corresponding pyridone acid of formula IIIb may be obtained.

As shown in Scheme II, a starting material alcohol of formula II may be obtained from a corresponding pyridone acid of formula IIIb and a corresponding amine of formula $R^1NH_2$. Thus by using a conventional method, the carboxy group of an acid of formula IIIb may be converted into a corresponding urethane, conveniently a benzyl urethane of formula IVa, for example as described in Example 1.f. by treatment with diphenylphosphoryl azide in an inert solvent, followed by treatment of the intermediate isocyanate with benzyl alcohol.

By formation of a corresponding amide of formula IVc, followed by intramolecular cyclization, an ester of formula IVa may be converted into a corresponding bicyclic compound of formula V. Conveniently, an ester of formula IVa is hydrolyzed to the corresponding acid of formula IVb, and the acid is coupled with an amine of formula $R^1NH_2$ to afford a corresponding amide of formula IVc, for example as described in Example 1.g.–1.h. in which $R^1$ is benzyl. An amide of formula IVc can be isolated and subsequently cyclized as described in Example 15.a.–15.b., or cyclized without isolation as described in Example 1.h., to give a compound of formula V. Removal of the protecting group Rp from a compound of formula V, yields a corresponding alcohol of formula II.

The trifluoromethyl amino alcohols required for the synthesis routes described above may be prepared by known procedures. For example, 3-amino-1,1,1,-trifluoro-4-methyl-2-pentanol (V, as its hydrochloride salt) conveniently may be obtained as described in U.S. Pat. No. 4,910,190 in Example 4 (as a single diastereomer) or Example 6 (as a single enantiomer of a single diastereomer). If it is desired to carry out a chiral synthesis of a compound of formula I, using the single enantiomer in a substantially enantiomerically pure form and using methods and conditions which avoid epimerization at the center indicated by "*" in formula I provide such a synthesis.

It may be desired optionally to use a protecting group during all or portions of the above described processes; the protecting group then may be removed when the final compound or a required starting material is to be formed. As will be clear to one skilled in the art, the order of steps in the sequences leading to the starting materials and products of the invention may be altered if appropriate considerations relative to coupling methods, racemization, deprotection methods, etc. are followed.

The utility of a compound of the invention or a pharmaceutically acceptable salt thereof (hereinafter, collectively referred to as a "Compound") may be demonstrated by standard tests and clinical studies, including those described below.

Inhibition Measurements:

The potency of a Compound to act as an inhibitor of human leukocyte elastase (HLE) on the low molecular weight peptide substrate methoxy-succinyl-alanyl-alanyl-prolyl-valine-p-nitroanilide is determined as described in U.S. Pat. No. 4,910,190. The potency of an inhibitor is evaluated by obtaining a kinetic determination of the dissociation constant, $K_i$, of the complex formed from the interaction of the inhibitor with HLE. If a Compound is found to be a "slow-binding" inhibitor of HLE, special methods of analysis to accurately determine $K_i$ values for the inhibition of HLE are carried out as described in U.S. Pat. No. 4,910,190. Although some of the Compounds of the invention wherein $R^1$ and $R^6$ are hydrogen exhibited $K_i$ values in the micromolar range, in general, the $K_i$ values for Compounds of the invention which were tested are generally on the order of $10^{-7}$M or much less. For example a $K_i$ of 44 nM was measured for the Compound of the invention described in Example 13.

Acute Lung Injury Model:

Animal models of emphysema include intratracheal (i.t.) administration of an elastolytic protease to cause a slowly progressive, destructive lesion of the lung. These lesions are normally evaluated a few weeks to a few months after the initial insult. However, these proteases also induce a lesion that is evident in the first few hours. The early lesion is first hemorrhagic, progresses to an inflammatory lesion by the end of the first 24 hours and resolves in the first week post insult. To take advantage of this early lesion, the following model was used.

Hamsters are first lightly anesthetized with Brevital. Phosphate buffered saline (PBS) pH 7.4, either alone or containing human leukocyte elastase (HLE), is then administered directly into the trachea. Twenty-four hours later the animals are killed and the lungs removed and carefully trimmed of extraneous tissue. Following determination of wet lung weight, the lungs are lavaged with PBS and total lavagable red and white cells recovered are determined. The values for wet lung weights, total lavagable red cells and total lavagable white cells are elevated in a dose-dependent manner following administration of HLE. Compounds that are effective elastase inhibitors can prevent or diminish the severity of the enzyme-induced lesion resulting in lower wet lung weight and reduced values for total lavagable cells, both red and white, relative to administration of HLE alone. Compounds can be evaluated by administering them intratracheally as solutions or suspensions in PBS, either with or at various times prior to the HLE challenge (400 µg), or by dosing them intravenously or orally as solutions at various times prior to the HLE challenge (100 µg) to determine their utility in preventing an HLE lesion. A solution of a Compound is conveniently prepared using 10% polyethylene glycol 400/PBS or 10% polyethylene glycol 400/water. For a Compound which is acidic or basic, base (e.g. sodium hydroxide solution) or acid (e.g. hydrochloric acid) may be added as indicated to achieve solution. Compounds of this invention produced statistically significant reductions in wet lung weight and total lavagable cells relative to HLE alone.

Acute Hemorrhagic Assay:

This assay relies on monitoring only the amount of hemorrhage in the lung following intratracheal administration of human neutrophil elastase (HNE). Hemorrhage is quantified by disrupting erythrocytes recovered in lung lavage fluid and comparing that to dilutions of whole hamster blood. The screening protocol, similar to that described in Fletcher etal., *American Review of Respiratory Disease* (1990), 141, 672–677, is as follows. Compounds demonstrated to be HNE inhibitors in vitro are conveniently prepared for dosing as described above for the Acute Lung Injury Model. The compounds are then dosed by mouth to male Syrian hamsters at a fixed time, such as 30 or 90 min, prior to intratracheal administration of 50 µg/animal of HNE in 300 µL phosphate buffered saline (PBS) pH 7.4. Four hours after enzyme administration, the animals are killed with an overdose of pentobarbital sodium, the thorax opened and the lungs and trachea removed. The excised lungs are layaged with three changes of 2 mL normal saline via a tracheal cannula. The recovered lavages are pooled, the volumes (about 5 mL) are recorded and the lavages stored at 4° C. until assayed. For calculation of the amount of blood in each sample, the thawed lavages and a sample of whole hamster blood are sonicated to disrupt erythrocytes and appropriately diluted into individual wells of a 96-well microtiter plate. The optical densities (OD) of the disrupted lavages and blood samples are determined at 405 nm. The (µL blood equivalents)/(mL lavage) are determined by comparing the OD of the test samples with the OD of the standard curve prepared from whole hamster blood. The total µL equivalents of blood recovered is determined by multiplying recovered lavage volume by the (µL blood equivalents)/(mL lavage) for each sample. Results are reported as % inhibition of hemorrhage with respect to PBS treated controls when the test compound is given at a specified dose and time prior to administration of HNE.

No overt toxicity was observed when Compounds of the invention were administered in the above in vivo tests.

It will be appreciated that the implications of a Compound's activity in the Acute Lung Injury Model or Acute Hemorrhagic Assay are not limited to emphysema, but, rather, that the test provides evidence of general in vivo inhibition of HLE.

Compounds of the present invention which were tested exhibited activity in at least one of the tests described above under Inhibition Measurement, Acute Lung Injury Model and Acute Hemorrhagic Assay. It should be noted that there was not always a direct correlation between the activities of the compounds measured as $K_i$ values in the Inhibition Measurement test and the reduced values for total lavagable cells and wet lung weights relative to the administration of HLE alone obtained in the Acute Lung Injury Model test or inhibition of hemorrhage in the Acute Hemorragic Assay.

According to a further feature of the invention, there is provided a pharmaceutical composition comprising a pharmaceutically effective amount of a Compound and a pharmaceutically acceptable diluent or carrier. As noted above, another feature of the invention is a method of using a Compound of the invention in the treatment of a disease or condition in a mammal, especially a human, in which HLE is implicated.

A Compound of the present invention may be administered to a warm-blooded animal, particularly a human, in need thereof for treatment of a disease in which HLE is implicated, in the form of a conventional pharmaceutical composition, for example as generally disclosed in U.S. Pat. No. 4,910,190. The preferred mode of administration may be via a powdered or liquid aerosol. In a powdered aerosol, a Compound of the invention may be administered in the same manner as cromolyn sodium via a 'Spinhaler' (a trademark) turbo-inhaler device obtained from Fisons Corp. of Bedford, Mass. at a rate of about 0.1 to 50 mg per capsule, 1 to 8 capsules being administered daily for an average human. Each capsule to be used in the turbo-inhaler contains the required amount of a Compound of the invention with the remainder of the 20 mg capsule being a pharmaceutically acceptable carrier such as lactose. In a liquid aerosol, a Compound of the invention may be administered using a nebulizer such as, for example, a 'Retec' (trademark) nebulizer, in which the solution is nebulized with compressed air. The aerosol may be administered, for example, at the rate of one to about eight times per day as follows: A nebulizer is filled with a solution of a Compound, for example 3.5 mL of solution containing 10 mg/mL; the solution in the nebulizer is nebulized with compressed air; and the patient breathes normally (tidal volume) for eight minutes with the nebulizer in his mouth.

Alternatively, the mode of administration may be oral or parenteral, including subcutaneous deposit by means of an osmotic pump. A compound of the invention may be conventionally formulated in an oral or parenteral dosage form by compounding about 10 to 250 mg per unit of dosage with conventional vehicle, excipient, binder, preservative, stabilizer, flavor or the like as called for by accepted pharmaceutical practice, e.g. as described in U.S. Pat. No. 3,755, 340. For parenteral administration, a 1 to 10 mL intravenous, intramuscular or subcutaneous injection would be given containing about 0.02 mg to 10 mg/kg of body weight of a compound of the invention 3 or 4 times daily. The injection would contain a compound of the invention in an aqueous isotonic sterile solution or suspension optionally with a preservative such as phenol or a solubilizing agent such as ethylenediaminetetraacetic acid (EDTA).

For parenteral administration or use in an aerosol, an 10 mg/mL aqueous formulation of an acidic Compound may be prepared, for example by dissolving the Compound (10 mg), dibasic sodium phosphate heptahydrate, USP (11.97 mg), monobasic sodium phosphate, USP (0.74 mg), sodium chloride, USP (4.50 mg) and sufficient 1N sodium hydroxide solution or 0.05M monobasic sodium phosphate solution to achieve pH 7.0–7.5 in sufficient water for injection, USP to afford 1.0 mL (1.01 g), followed by aseptic filtration, and sterile storage using standard procedures.

In general, a Compound of the invention will be administered to humans at a daily dose in the range of, for example, 5 to 100 mg of the Compound by aerosol or 50 to 1000 mg intravenously, or a combination of the two. However, it readily will be understood that it may be necessary to vary the dose of the Compound administered in accordance with well known medical practice to take account of the nature and severity of the disease under treatment, concurrent therapy, and the age, weight and sex of the patient receiving treatment. It similarly will be understood that generally equivalent amounts of a pharmaceutically acceptable salt of the Compound also may be used. Protocols for the administration of the HLE inhibitor and evaluation of the patients are described in the European Pat. No. Applications with Publication Numbers 458535, 458536, 458537, and 463811 for the treatment or prevention of cystic fibrosis, ARDS, bronchitis, and hemorrhage associated with acute non-lymphocytic leukemia or its therapy, respectively; and a Compound of the invention may be used similarly for the treatment of those diseases and conditions either alone or in combination with another therapeutic agent customarily indicated for the treatment of the particular condition. For therapeutic or prophylactic treatment of a vascular disease or related condition in a mammal in which neutrophils are involved or implicated, a Compound of the invention may conveniently be administered by a parenteral route, either alone or simultaneously or sequentially with other therapeutically active agents customarily administered for the condition.

The invention will now be illustrated by the following non-limiting examples in which, unless stated otherwise:

(i) temperatures are given in degrees Celsius (° C.); operations were carried out at room or ambient temperature, that is, at a temperature in the range of 18°–25° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60° C.;

(iii) chromatography means 'flash chromatography' (method of Still) carried out on Merck Kieselgel (Art 9385 from E. Merck, Darmstadt, Germany), elution using both step and ramp gradients is denoted by the parenthetical term "gradient" followed by the initial and final solvent ratios; thin layer chomatography (TLC) was carried out on 0.25 mm silica gel GHLF plates (Art 21521 from Analtech, Newark, Del., USA);

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory nuclear magnetic resonance (NMR) spectra; and, where examined, were substantially pure by HPLC;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylstlane (TMS) as an internal standard, determined at 250 MHz usinE DMSO-$d_6$ as solvent; conventional abbreviations for signal shape are used; for AB spectra the directly observed shifts are reported;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms;

(xii) mass spectra (MS) were run with an electron energy of 70 electron volts in the chemical ionizaton mode using a direct exposure probe; where indicated ionization was effected by electron impact (EI) or fast atom bombardment (FAB); generally, only peaks which indicate the parent mass are reported; and (xiii) when high pressure liquid chromatography (HPLC) data is reported, $t_R$ (retention time) is given in min, FR (flow rate) is given in ml/min, Col A is a Zorbax (trademark) ODS analytical column (4.6 mm×25 cm) and Col B is a Phenomenex (trademark) Zorbax (trademark) C-8 analytical column (4.6 mm×35 cm); solvent system A is water:acetonitrile:tetrahydrofuran:trifluoroacetic acid (55:35:15:0.1).

EXAMPLE 1

2-(3-Benzyl-2,4,8-trioxo-1,2,3,4,7,8-hexahydropyrido[3,4-d]pyrimidin-7-yl)-N-(3,3,3-trifluoro-1-isopropyl-2-oxopropyl)acetamide.

A solution of the alcohol from Example 1.i. (0.400 g) in dimethyl sulfoxide:toluene (1:1, 8 mL) was treated with 1-(3-dimethylaminopropyl)- 3-ethylcarbodiimide hydrochloride (1.59 g) followed by 2,2-dichloroacetic acid (0.274 mL). The reaction mixture was stirred for 5 hours and partitioned between chloroform and 1N hydrochloric acid. The organic layer was washed (1N hydrochloric acid, saturated sodium bicarbonate, brine), dried and evaporated. The product was purified by chromatography, eluting with methanol:chloroform (3:97). The resulting material was purified by chromatography, eluting with methanol:chloroform (gradient, 1:99, 1.5:98.5, 2:98), to afford the title compound (0.156 g) as a white solid; TLC: $R_f$=0.55, methanol:chloroform (5:95); HPLC, $t_R$=8.00, Col A, FR=2, water:acetonitrile (7:3); MS: m/z=479 (M+1). Analysis for $C_{22}H_{21}F_3N_4O_5$: Calculated: C, 55.23; H, 4.42; N, 11.71; Found: C, 55.58; H, 4.69; N, 11.36.

The alcohol used in Example 1 was prepared as follows:

a. 2-Phthalimido-N-(3,3,3-trifluoro-2-hydroxy-1-isopropylpropyl)acetamide.

A solution of N-phthaloylglycine (34.0 g) and 4-methylmorpholine (39.1 mL) at –40 °C. was treated dropwise with isobutyl chloroformate (22.1 mL) and stirred between –20° and –40 °C. for 1.5 hours. 3-amino-1,1,1-trifluoro-4-methyl-2-pentanol hydrochloride (33.6 g) was added and the solution was allowed to warm to room temperature. The solution was stirred for 1.5 hours, diluted with ethyl acetate, washed (1N hydrochloric acid, 1N NaOH, brine), dried and evaporated to afford the acetamide (47.2 g) as a white solid; TLC: $R_f$=0.30, methanol:chloroform (3:97); MS: m/z=359 (M+1).

b. N-(2-tert-Butyldimethylsilyloxy-3,3,3-trifluoro-1-isopropyl-propyl)-2-phthalimidoacetamide.

A solution of the alcohol from Example 1.a. (47.2 g) and 2,6-utidine (30.7 mL) in tetrahydrofuran (600 mL) at 0° C. was treated dropwise with a solution of tert-butyldimethylsilyl trifluoromethanesulfonate (45.4 mL) in tetrahydrofuran (50 mL) and stirred for 16 hours at room temperature. The resulting mixture was evaporated, taken up in ethyl acetate, washed (1N hydrochloric acid, 1N NaOH, brine), dried and evaporated to afford the ether (65.3 g, more than 100%) as a white solid; TLC: $R_f$=0.54, hexanes:acetone (2:1); MS: m/z=473(M+1).

c. 2-Amino-N-(2-tert-butyldimethylsilyloxy-3,3,3-trifluoro-1-isopropylpropyl)acetamide.

A solution of product from Example 1.b. (62.3 g) in ethanol (1.30 L) was heated to reflux, treated with hydrazine hydrate (19.2 mL) and refluxed for 3 hours. The mixture was acidified (pH 2) with 1N hydrochloric acid, refluxed for 1 hour, cooled to 0° C., filtered and evaporated. The residue was taken up in ethyl acetate, washed (1N NaOH until the pH exceeded 8.0, brine), dried and evaporated. The product was purified by chromatography, eluting with methanol:dichloromethane (gradient, 2:98, 5:95), to afford the amine (43.8 g) as clear oil; TLC: $R_f$=0.68, hexanes:acetone (3:2); MS: m/z=343(M+1).

d. 2-(4-Ethoxycarbonyl-3-methoxycarbonyl-2-oxo-1,2-dihydro-1-pyridyl)-N-( 2-tert-butyldimethylsilyloxy-3,3,3-trifluoro-1-isopropylpropyl)acetamide.

A solution of the product of Example 1.k. (27.6 g) and the product of Example 1.c. (30.1 g) in ethanol (140 mL) was heated at reflux for 16 hours and evaporated. The residue was taken up in ethyl acetate, and was washed (1N hydrochloric acid, brine), dried ($K_2CO_3$:$Na_2SO_4$, 1:1) and evaporated. The residue was taken up in ether, washed (1N hydrochloric acid, brine), dried ($K_2CO_3$: $Na_2SO_4$, 1:1) and evaporated to afford the pyridone (34.5 g) as a yellow foam; TLC: $R_f$=0.68, hexanes:acetone (1:1); MS: m/z=551(M+1).

e. 2-(3-Carboxy-4-ethoxycarbonyl-2-oxo-1,2-dihydro-1-pyridyl)-N-(2-tert-butyldimethylsilyloxy-3,3,3-trifluoro-1-isopropylpropyl)acetamide.

A solution of LiI (20.0 g) in refluxing pyrtdine (200 mL) was treated dropwise with a solution of the product from Example 1.d. (20.5 g) in pyridine (200 mL). The solution was heated at reflux for 1 hour and evaporated. The residue was taken up in ethyl acetate, and was washed (1N hydrochloric acid, brine), dried and evaporated to afford the acid (19.2 g) as an orange foam; TLC: $R_f$=0.63, chloroform:methanol:acetic acid (95:5:1); MS: m/zz537(M+1).

f. 2-(3-Benzyloxycarbonylamino-4-ethoxycarbonyl-2-oxo-1,2-dihydro-1-pyridyl)-N-(2-tert-butyldimethylsilyloxy-3,3,3-trifluoro-1-isopropylpropyl)acetamide.

A solution of the acid from Example 1.e. (15.0 g) in p-dioxane (150 mL) was treated with triethylamine (4.70 mL) and diphenylphosphoryl azide (6.70 mL). The solution was heated at reflux for 2 hours and treated with benzyl alcohol (3.18 mL). The solution was heated for 16 hours, partitioned between ethyl acetate and 1N hydrochloric acid, washed (1N hydrochloric acid, 1N NaOH, brine), dried and evaporated. The residue was triturated with hexanes:acetone and filtered to afford the benzyl urethane (4.80 g) as white crystals. The filtrate was evaporated and the residue purified by chromatography, eluting with acetone:hexanes (gradient, 4:1, 3:1, 2:1), to afford additional product (7.20 g) as a white solid; TLC: $R_f$=0.22, hexanes:acetone (8:2); MS: m/z=642(M+1).

g. 2-(3-Benzyloxycarbonylamino-4-carboxy-2-oxo-1,2-dihydro-1-pyridyl)-N-(2-tert-butyldimethylsilyloxy-3,3,3-trifluoro-1-isopropylpropyl)acetamide.

A solution of the ester from Example 1.f. (11.80 g) in ethanol (250 mL) was treated with a solution of potassium hydroxide (1.13 g) in water (125 mL). The solution was stirred at room temperature for 3 hours, treated with an additional solution of KOH (0.57 g) in water (50 mL), stirred at room temperature for 1 hour, warmed to 35° C. and cooled to room temperature. The solution was acidified (pH 2) with 1N hydrochloric acid, diluted with brine and extracted with chloroform. The combined organic extracts were dried and evaporated. The product was recrystallized from ethanol:water to afford the acid (8.75 g) as off-white crystals; TLC: $R_f$=0.23, methanol:chloroform:acetic acid (5:95:1); MS: m/z=614(M+1).

h. 2-(3-Benzyl-2,4,8-trioxo-1,2,3,4,7,8-hexahydropyrido[3,4-d]-pyrimidin- 7-yl)-N-(2-tert-butyldimethylsilyloxy-3,3,3-trifluoro-1-isopropylpropyl)acetamide.

A solution of the acid from Example 1.g. (0.500 g), benzylamine (0.178 mL), and 1-hydroxybenzotriazole hydrate (0.220 g) in dimethylformamide (5 mL) was treated with 1-(3-dimethylamino-propyl)-3-ethylcarbodiimide hydrochloride (0.172 g) and stirred for 16 hours. The mixture was taken up in ethyl acetate, washed (1N hydrochloric acid, 1N NaOH, brine), dried and evaporated. The residue was dissolved in dimethylformamide (5 mL), heated at 120° C. for 2 hours, taken up in ethyl acetate, washed (1N hydrochloric acid, 1N NaOH, brine), dried and evaporated to afford the bicyclic compound (0.490 g); TLC: $R_f$=0.55, methanol:chloroform (5:95); MS: m/z=595(M+1).

i. 2-(3-Benzyl-2,4,8-trioxo-1,2,3,4,7,8-hexahydropyrido[3, 4-d]-pyrimidin- 7-yl)-N-(3,3,3-trifluoro-2-hydroxy-1-isopropylpropyl)acetamide.

A solution of the product of Example 1.h. (0.480 g) in tetrahydrofuran (10 mL) was treated with tetrabutylammonium fluoride (0.82 mL, 1.0M in THF), and stirred at room temperature for 2 hours. The solution was partitioned between ethyl acetate and 1N hydrochloric acid, and the organic layers were washed (1N hydrochloric acid, 1N NaOH), and discarded. The combined aqueous washes were made basic with 1N NaOH, extracted with chloroform and the chloroform layers were dried ($K_2CO_3/Na_2SO_4$, 1:1) and evaporated to afford the alcohol (0.445 g, greater than 100%) as a solid; TLC: $R_f$=0.40, methanol:chloroform (5:95); MS: m/z=481(M+1).

The intermediate dimethyl (2-ethoxycarbonyl-3-dimethylamino-2-propenylidene)malonate used in Example 1.d. was prepared as follows.

j. Dimethyl (2-ethoxycarbonylethylidene)malonate

A suspension of anhydrous zinc chloride (258 g) in acetic anhydride (474 g) was stirred for 2 hours. The solution was decanted and treated dropwise with ethyl pyruvate (120 g) followed by dimethyl malonate (136 g). The resulting mixture was allowed to reflux for 2 hours. The material was purified by vacuum distillation (bp 136° C., 101 Pa) to afford the product (182 g) as a light yellow liquid; TLC: $R_f$=0.25, hexanes:acetone (9:1); MS: m/z=231(M+1).

k. Dimethyl (2-ethoxycarbonyl-3-dimethylamino-2-propenylidene)malonate.

A solution of the product of Example 1.j. (38.0 g) and N,N-dimethylformamide diethyl acetal (29.1 mL) in dimethylformamide (57 mL) was heated at 80° C. for 3 hours and partitioned between brine and ethyl acetate. The ethyl acetate layer was washed with brine and the combined aqueous washes were extracted with ethyl acetate. The combined organic layers were dried ($Na_2SO_4$), and evaporated. The product was crystallized from carbon tetrachloride (550 mL) to afford the diene (37.5 g) as a yellow solid; TLC: $R_f$=0.54, chloroform:acetone (15:1); MS: m/z= 286(M+1).

2-(4-Ethoxycarbonyl-3-methoxycarbonyl-2-oxo-1,2-dihydro-1-pyridyl)-N-( 2-tert-butyldimethylsilyloxy-3,3,3-trifluoro-1-isopropylpropyl)acetamide used in Example 1.d. can alternatively be prepared as follows.

l. 2-Chloro-N-(3,3,3-trifluoro-2-hydroxy-1-isopropylpropyl)acetamide.

A solution of 3-amino-1,1,1-trifluoro-4-methyl-2-pentanol hydrochloride (10.0 g) and 4-methylmorpholine (10.9 mL) in tetrahydrofuran (240 mL) at 0° C. was treated dropwise with a solution of chloroacetyl chloride (3.85 mL) in tetrahydrofuran (20 mL). The solution was stirred at 0° C. for 3 hours and evaporated. The residue was taken up in ethyl acetate, washed (1N hydrochloric acid, 1N NaOH, brine), dried and evaporated to afford the amide (12.2 g) as a yellow oil; TLC: $R_f$=0.75, methanol:chloroform (5:95); MS: m/z=248(M+1 for $^{35}$Cl).

m. N-(2-tert-Butyldimethylsilyloxy-3,3,3-trifluoro-1-isopropyl-propyl)-2-chloroacetamide.

A solution of the alcohol of Example 1.1. (11.4 g) and 2,6-lutidine (10.7 mL) in dichloromethane (46 mL) was treated dropwise with tert-butyldimethylsilyl trifluoromethanesulfonate (15.9 mL). The solution was stirred for 3 hours at room temperature, diluted with ethyl acetate, washed (1N hydrochloric acid, 1N NaOH, brine), dried and evaporated. The product was purified by chromatography, eluting with hexanes:ethyl acetate (gradient, 100:0, 9:1, 8:2), to afford the silyl ether (10.3 g) as a white solid; TLC: $R_f$=0.62, hexanes:ethyl acetate (4:1); MS: m/z=362(M+1 for $^{35}$Cl).

n. N-(2-tert-Butyldimethylsilyloxy-3,3,3-trifluoro-1-isopropyl-propyl)-2-iodoacetamide.

A solution of sodium iodide (8.45 g) and the product of Example 1.m. (5.10 g) in acetone (56 mL) was stirred at room temperature for 16 hours and was partitioned between ethyl acetate and water. The organic layer was washed (saturated sodium bisulfite, brine), dried and evaporated to afford the iodide (6.12 g) as a white solid; TLC: $R_f$=0.37, hexanes:ethyl acetate (9:1); MS: m/z=454(M+1).

o. 2-(4-Ethoxycarbonyl-3-methoxycarbonyl-2-oxo-1,2-dihydro-1-pyridyl)-N-( 2-tert-butyldimethylsilyloxy-3,3,3-trifluoro-1-isopropylpropyl)acetamide.

A solution of 4-ethoxycarbonyl-3-methoxycarbonyl-2-pyridone (6.2 g) and the product from Example 1.n. (18.1 g) in dimethylformamide (80 mL) was treated with 1,8-diazabicyclo[5.4.0]-undec- 7-ene (6.47 mL) and stirred at room temperature for 24 hours. The reaction mixture was diluted with ethyl acetate, washed (1N hydrochloric acid, brine, 1N NaOH, brine), dried ($K_2CO_3$: $Na_2SO_4$, 1:1) and evaporated. The product was purified by chromatography, eluting with acetone:hexanes (1:4), to afford the amide (8.82 g) as a light yellow solid; TLC: $R_f$=0.55, acetone:hexanes (3:7); MS: m/z=551(M+1).

The intermediate 4-ethoxycarbonyl-3-methoxycarbonyl-2- pyridone used in Example 1.o. was prepared as follows:

p. 4-Ethoxycarbonyl-1-(4-methoxybenzyl)-3-methoxycarbonyl-2-pyridone.

A solution of the product of Example 1.k. (37.2 g) in ethanol (186 mL), was treated dropwise with p-methoxybenzylamine (18.8 mL) and heated at reflux for 1.1 hours. The solution was evaporated; and the residue was taken up in ethyl acetate, washed (1N hydrochloric acid, brine), dried ($K_2CO_3$: $Na_2SO_4$, 1:1), and evaporated to afford the 1-(4-methoxybenzyl) compound (45.6 g) as a brown gum; TLC: $R_f$=0.42, chloroform:acetone (15:1); MS: m/z=346(M+1).

q. 4-Ethoxycarbonyl-3-methoxycarbonyl-2-pyridone.

A solution of the product of Example 1.p. (24.0 g) in acetonitrile:water (275 mL, 10:1) was treated with ceric ammonium nitrate (190 g) and stirred at room temperature for 0.5 hour. The solution was diluted with chloroform (1 L), filtered, and the organic filtrate was washed (1N hydrochloric acid, brine), dried and evaporated. The product was purified by chromatography, eluting with chloroform:methanol (gradient, 100:0, 95:5), to afford the pyridone (6.3 g) as a white solid; TLC: $R_f$=0.49, methanol:chloroform (9:1); MS: m/z=266(M+1).

EXAMPLES 2–13

Using procedures similar to that described in Example 1 the following compounds of formula I wherein $R^2$ is hydrogen, $R^0$ is isopropyl and $R^1$ has the indicated value were prepared by oxidation of the corresponding alcohols of formula II, with exceptions as noted.

Example 2

$R^1$=methyl: The product was isolated by evaporation and purified by chromatography, eluting with chloroform:methanol (gradient, 100:0, 98:2, 97:3), to afford the title compound (0.106 g) as a white solid; HPLC, $t_R$=7.01, Col A, FR=2, water:acetonitrile (5:1); MS: m/z=403(M+1). Analysis for $C_{16}H_{17}F_3N_4O_5$.0.65 $H_2O$: Calculated: C, 46.41; H, 4.45; N, 13.53; Found: C, 46.86; H, 4.58; N, 13.15.

Example 3

$R^1$=hydrogen: No extractive work-up was used. The reaction mixture was diluted with chloroform and purified by chromatography, eluting with chloroform:methanol (gradient, 100:0, 97.5:2.5, 95:5, 90:10), to afford the title compound (0.045 g) as a white solid; HPLC, $t_R$=5.20, Col A, FR=1.5, water:acetonitrile (85:15); MS: m/z=389(M+1). Analysis for $C_{15}H_{15}F_3N_4O_5$·0.70 $H_2O$: Calculated: C, 44.93; H, 4.12; N, 13.97; Found: C, 45.31; H, 4.51; N, 13.39.

Example 4

$R^1$=1-naphthylmethyl: The reactants were added at 0° C. and warmed to room temperature. The reaction mixture was diluted with chloroform, washed (1N hydrochloric acid, 1N NaOH, brine), and the combined aqueous washes were acidified with 1N hydrochloric acid and extracted with ethyl acetate. The combined chloroform and ethyl acetate extracts were washed (brine), dried and evaporated. The material was purified by chromatography, eluting with hexanes:acetone (gradient, 4:1, 3:1, 2:1). A second purification by chromatography, eluting with dichloromethane:methanol (98:2), afforded the title compound (0.200 g) as a white foam; TLC: $R_f$=0.38, chloroform:methanol (95:5); HPLC, $t_R$=6.44, Col A, FR=1, water:acetonitrile (1:1); MS: m/z=529(M+1). Analysis for $C_{26}H_{23}F_3N_4O_5$·1.20 $H_2O$: Calculated: C, 56.77; H, 4.65; N, 10.18; Found: C, 56.98; H, 4.50; N, 10.01.

Example 5

$R^1$=phenyl: Ethyl acetate was used instead of chloroform and no sodium bicarbonate wash was used in the extractive work-up. The product was purified by chromatography, eluting with chloroform:ethanol (96:4), to afford the title compound (0.120 g) as a white foam; TLC: $R_f$=0.23, chloroform:methanol (95:5); HPLC, $t_R$=7.06, Col A, FR=1.5, water:acetonitrile (3:1); MS: m/z=465(M+1). Analysis for $C_{21}H_{19}F_3N_4O_5$· 0.75 $H_2O$: Calculated: C, 52.78; H, 4.32; N, 11.72; Found: C, 52.85; H, 4.54; N, 11.14.

Example 6

$R^1$=phenethyl: The reactants were added at 0° C. and warmed to room temperature. Ethyl acetate was used instead of chloroform and no sodium bicarbonate wash was used in the extractive work-up. The product was purified by chromatography, eluting with chloroform:methanol (98:2). The isolated material was repurified by chromatography, eluting with chloroform:methanol (99:1). A final purification by chromatography, eluting with hexanes:acetone (3:1), afforded the title compound (0.150 g) as a white solid; TLC: $R_f$=0.43, chloroform:methanol (95:5); HPLC, $t_R$=5.98, Col A, FR=1.5, water:acetonitrile (3:2); MS: m/zz493(M+1). Analysis for $C_{23}H_{23}F_3N_4O_5$· 0.80 $H_2O$: Calculated: C, 54.50; H, 4.89; N, 11.05; Found: C, 54.51; H, 4.86; N, 10.82.

Example 7

$R^1$=2-(1-naphthyl)ethyl: Ethyl acetate was used instead of chloroform and no sodium bicarbonate wash was used in the extractive work-up. The product was purified by triturating with methanol to afford the title compound (0.101 g) as a white solid; TLC: $R_f$=0.47, chloroform:methanol (95:5); HPLC, $t_R$=11.73, Col A, FR=1.5, water:acetonitrile (3:2); MS: m/z=543(M+1). Analysis for $C_{27}H_{25}F_3N_4O_5$·0.50 $H_2O$: Calculated: C, 58.80; H, 4.75; N, 10.16; Found: C, 58.76; H, 4.74; N, 9.58.

Example 8

$R^1$=2-phenylcyclopropyl: No sodium bicarbonate wash was used in the extractive work-up. The product was purified by chromatography, eluting with hexanes:acetone (gradient, 3:1, 2:1, 1:**), to afford the title compound (0.110 g) as a white foam; TLC: $R_f$=0.42, chloroform:methanol (97:3); HPLC, $t_R$=5.95, Col A, FR=1.5, water:acetonitrile (2:3); MS: m/z=505(M+1). Analysis for $C_{24}H_{23}F_3N_4O_5$·0.50 $H_2O$: Calculated: C, 56.14; H, 4.71; N, 10.91; Found: C, 56.15; H, 4.86; N, 10.19.

Example 9

$R^1$=phenacyl: No sodium bicarbonate wash was used in the extractive work-up. The product was purified by chromatography, eluting with dichloromethane:methanol (gradient, 98:2, 97:3, 95:5), and triturated with ethanol and ether to afford the title compound (0.110 g) as a solid; TLC: $R_f$=0.26, chloroform:methanol (95:5); HPLC, $t_R$=8.70, Col A, FR=1.5, water:acetonitrile (7:3); MS: m/z=507(M+1). Analysis for $C_{23}H_{21}F_3N_4O_6$·0.20 $H_2O$·0.40 $C_2H_5OH$: Calculated: C, 54.09; H, 4.54; N, 10.6; Found: C, 54.14; H, 4.64; N, 10.50.

Example 10

$R^1$=α,α-dimethylphenethyl: No sodium bicarbonate wash was used in the extractive work-up. The product was purified by chromatography, eluting with hexanes:acetone (gradient, 4:1, 3:1, 2:1), to afford the title compound (0.190 g) as a brown foam; TLC: $R_f$=0.66, chloroform:methanol (95:5); HPLC, $t_R$=6.78, Col A, FR=1.5, water:acetonitrile (55:45); MS: m/z=521(M+1). Analysis for $C_{25}H_{27}F_3N_4O_5$: Calculated: C, 57.59; H, 5.23; N, 10.76; Found: C, 57.55; H, 5.46; N, 10.41.

Example 11

$R^1$=tert-butoxycarbonylmethyl: No sodium bicarbonate wash was used and 2N hydrochloric acid:brine (1:1) was used instead of 1N hydrochloric acid in the extractive work-up. The product was purified by chromatography, eluting with dichloromethane:methanol (98:2), to afford the title compound (0.030 g) as an off-white foam; TLC: $R_f$=0.48, chloroform:methanol (95:5); HPLC, $t_R$=9.58, Col A, FR=1.5, water:acetonitrile (7:3); MS: m/z=447. Analysis for $C_{21}H_{25}F_3N_4O_7$·0.20 $C_6H_{14}$: Calculated: C, 51.31; H, 5.39; N, 10.78; Found: C, 51.08; H, 5.30; N, 10.34.

Example 12

$R^1$=methoxycarbonylmethyl: No sodium bicarbonate wash was used and 2N hydrochloric acid:brine (1:1) was used instead of 1N hydrochloric acid in the extractive work-up. The combined aqueous washes were saturated with NaCl, extracted with chloroform and the combined chloroform layers were dried and evaporated. The product was purified by chromatography, eluting with dichloromethane:methanol (gradient, 98:2, 97:3), to afford the title compound (0.110 g) as an off-white foam; TLC: $R_f$=0.46, chloroform:methanol (95:5); HPLC, $t_R$=7.15, Col A, FR=1.0, water:acetonitrile (3:1); MS: m/z=461(M+1). Analysis for $C_{18}H_{19}F_3N_4O_7$: Calculated: C, 46.96; H, 4.16; N, 12.17; Found: C, 47.29; H, 4.40; N, 11.76.

Example 13

$R^1$=benzyloxycarbonylmethyl: No sodium bicarbonate wash was performed and 2N hydrochloric acid:brine (1:1) was used instead of 1N hydrochloric acid in the extractive work-up. The product was purified by chromatography, eluting with dichloromethane:methanol (gradient, 98:2, 97:3), to afford the title compound (0.210 g) as an off-white foam; TLC: $R_f$=0.47, chloroform:methanol (95:5); HPLC, $t_R$=8.91, Col A, FR=1.5, water:acetonitrile (3:1); MS: m/z=537(M+1). Analysis for $C_{24}H_{23}F_3N_4O_7$: Calculated: C, 53.73; H, 4.32; N, 10.44; Found: C, 53.44; H, 4.44; N, 10.30.

The intermediate alcohols, used in Examples 2–13, were prepared as follows:

EXAMPLES 2.a.–13.a.

Using procedures similar to that outlined in Example 1.h., 2-(3-benzyloxycarbonylamino-4-carboxy-2-oxo-1,2-dihydro-1-pyridyl)-N-( 2-tert-butyldimethylsilyloxy-3,3,3-trifluoro-1-isopropylpropyl)acetamide was converted into the following tert-butyldimethylsilyl ethers of the corresponding alcohols formula II wherein $R^2$ is hydrogen, $R^0$ is isopropyl and $R^1$ is the indicated group, with exceptions as noted.

Example 2.a.

$R^1$=-methyl: Using methylamine hydrochloride (4 equivalents) instead of benzylamine and using 4-methylmorpholine (5 equivalents) as an acid scavenger. The product was purified by chromatography, eluting with chloroform:methanol (gradient, 100:0, 99:1, 98:2, 97:3, 95:5), to afford the tert-butyldimethylsilyl ether (0.344 g) as a white solid; TLC: $R_f$=0.63, methanol:chloroform (5:95); MS: m/z=519(M+1).

Example 3.a.

$R^1$=hydrogen: 1-Hydroxybenzotriazole:ammonia complex was used instead of 1-hydroxybenzotriazole and benzylamine. Chloroform was used as the extraction solvent instead of ethyl acetate. The final product was isolated by evaporation, after heating at 120° C. in dimethylformamide and was purified by chromatography, eluting with chloroform:methanol (gradient, 100:0, 97.5:2.5, 95:5), to afford the tert-butyldimethylsilyl ether (0.285 g) as an off-white solid; TLC: $R_f$=0.43, methanol:chloroform (1:9); MS: m/z=505(M+1).

Example 4.a.

$R^1$=1-naphthylmethyl: 1-Napthylmethylamine was used instead of benzylamine and no 1N NaOH wash was used in the second extractive work-up. The product (0.580 g) was used without further purification; TLC: $R_f$=0.71, chloroform:methanol (97:3); MS: m/z=645(M+1).

Example 5.a.

$R^1$=-phenyl: No 1N NaOH wash was used in the second extractive work-up and aniline was used instead of benzylamine. The product (0.450 g) was used without further purification; TLC: $R_f$=0.33, hexanes:acetone (2:1); MS: m/z=581(M+1).

Example 6.a.

$R^1$=phenethyl: No 1N NaOH wash was used in the second extractive work-up, 2-phenethylamine was used instead of benzylamine, and the product (0.510 g) was used without further purification; TLC: $R_f$=0.75, chloroform:methanol (97:3); MS: m/z=609(M+1).

Example 7.a.

$R^1$=2-(1-naphthyl)ethyl: 2-(1-Naphthyl)ethylamine was used in place of benzylamine. In the second extractive work-up, no 1N NaOH wash was used and water was used instead of 1N hydrochloric acid. The product (0.480 g) was used without further purification; TLC: $R_f$=0.57, chloroform:methanol (97:3); MS: m/z=659(M+1).

The intermediate 2-(1-naphthyl)ethylamine was prepared as follows.

A suspension of 2-(1-napthyl)acetamide (1.85 g) in tetrahydrofuran (30 mL) was treated dropwise with lithium aluminum hydride (20 mL, 1.0M in THF). After gas evolution ceased, the mixture was heated to reflux for 2 hours, cooled to 0° C., treated dropwise with water (2.9 mL) and filtered. The liltrate was evaporated and purified by chromatography, eluting with chloroform:methanol:ammonium hydroxide (gradient, 100:0:0, 9:1:0, 9:1:0.1), to afford the product (0,240 g) as a semisolid; TLC: $R_f$=0.09, chloroform:methanol (95:5); MS: m/z=172(M+1).

Example 8.a.

$R^1$=2-phenylcyclopropyl: 2-Phenylcyclopropylamine hydrochloride was used instead of benzylamine and 4-methylmorpholine was used as an acid scavenger (2.1 equivalents). In the second extractive work-up, no 1N NaOH wash was used and water was used instead of 1N hydrochloric acid. The product was triturated with methanol:ether to afford the tert-butyldimethylsilyl ether (0.300 g,); TLC: $R_f$=0.51, chloroform:methanol (97:3); MS: m/z=621(M+1).

Example 9.a.

$R^1$=phenacyl: Phenacylamine was used instead of benzylamine. In the second extractive work-up, no 1N NaOH wash was used and water was used instead of 1N hydrochloric acid. The product (0.490 g) was used without further purification; TLC: $R_f$=0.50, chloroform:methanol (97:3); MS: m/z=623(M+1).

Example 10.a.

$R^1$=α,α-dimethylphenethyl: α,α-Dimethylphenethylamine was used instead of benzylamine. In the second extractive work-up, no 1N NaOH wash was used and water was used instead of 1N hydrochloric acid. The product (0.440 g) was used without further purification; TLC: $R_f$=0.74, chloroform:methanol (97:3); MS: m/z=637(M+1).

Example 11.a.

$R^1$=tert-butoxycarbonylmethyl: tert-Butyl glycine was used instead of benzylamine. In the second extractive work-up, no 1N NaOH wash was used and water was used instead of 1N hydrochloric acid. The product (0.420 g) was used without further purification; TLC: $R_f$=0.59, chloroform:methanol (97:3); MS: m/z=619(M+1).

Example 12.a.

$R^1$=methoxycarbonylmethyl: Methyl glycine hydrochloride was used instead of benzylamine and 4-methylmorpholine (2.1 equivalents) was used as an acid scavenger. In the second extractive work-up, no 1N NaOH wash was used and water was used instead of 1N hydrochloric acid. The product (0.390 g) was used without further purification; TLC: $R_f$=0.55, chloroform:methanol (97:3); MS: m/z=557(M+1).

Example 13.a.

$R^1$=benzyloxycarbonylmethyl: Benzyl glycine hydrochloride was used instead of benzylamine, and 4-methylmorpholine (2.1 equivalents) was used as an acid scavenger. In the second extractive work-up, no 1N NaOH wash was used and water was used instead of 1N hydrochloric acid. The product (0.550 g) was used without further purification; TLC: $R_f$=0.82, chloroform:methanol (95:5); MS: m/z=653(M+1).

EXAMPLES 2.b.–13.b.

Using the procedures described, the following alcohols of formula I wherein $R^2$ is hydrogen, $R^0$ is isopropyl and $R^1$ is the indicated group were prepared from the corresponding tert-butyldimethylsilylethers prepared in Examples 2.a.–13.a.

Example 2.b.

$R^1$=methyl: Using a procedure similar to that described in Example 1.i., except employing an extractive work up, followed by evaporation, the product of Example 2.a. was converted to the alcohol which was purified by chromatography, eluting with methanol:chloroform (gradient, 0:100, 3:97), to afford the product (0.243 g) as a white solid; TLC: $R_f$=0.25, methanol:chloroform (5:95); MS: m/z=405(M+1). Analysis for $C_{16}H_{19}N_4O_5F_3$: Calculated: C, 47.53; H, 4.74; N, 13.9; Found: C, 47.24; H, 4.81; N, 13.52.

Example 3.b.

$R^1$=hydrogen: A solution of the product of Example 3.a. (0.270 g) in acetonitrile:tetrahydrofuran (7 mL, 6:1) was treated with HF (0.535 mL, 50% aqueous), stirred for 19 hours, treated with additional HF (0.535 mL) stirred for 2 hours, treated with additional HF (1 mL), stirred for 3 hours, diluted with methanol (5 mL), stirred for 16 hours, treated with silica gel (1 g) and evaporated. The residue was purified by chromatography, with chloroform:methanol (gradient, 100:0, 97.5:2.5, 95:5, 0:100) as the eluent, to afford the alcohol (0.170 g) as a white solid, which was used without further characterization.

Example 4.b.

$R^1$=1-naphthylmethyl: A solution of the product of Example 4.a. (0.570 g) in tetrahydrofuran (9 mL) was treated with tetrabutylammonium fluoride (1.33 mL, 1.0M in THF), stirred at 0° C. for 1 hour, diluted with ethyl acetate, washed (1N hydrochloric acid, brine, saturated sodium bicarbonate, brine), dried and evaporated. The product was purified by chromatography, eluting with chloroform:methanol (97:3), and crystallized from chloroform:methanol, to afford the alcohol (0.443 g) as a solid; TLC: $R_f$=0.18, methanol:chloroform (3:97); MS: m/z=531(M+1).

Example 5.b.

$R^1$=phenyl: The product from Example 5.a. was subjected to a procedure similar to that described in Example 4.b., except that sodium bicarbonate was not used in the extractive work-up, and the combined aqueous washes were saturated with sodium chloride, extracted with chloroform, and the combined ethyl acetate and chloroform layers were dried and evaporated. The residue was purified by chromatography, eluting with chloroform:methanol (95:5), to afford the alcohol (0.340 g) as a white solid; TLC: $R_f$=0.19, chloroform:methanol (95:5); MS: m/z=467(H+1).

Example 6.b.

$R^1$=phenethyl: Using a procedure similar to that described in Example 4.b., except that sodium bicarbonate was not used in the extractive work-up, the product of Example 6.a. was converted into material which was purified by chromatography, eluting with chloroform:methanol (97:3), to afford the alcohol (0.300 g) as a solid; TLC: $R_f$=0.16, chloroform:methanol (97:3); MS: m/z=495(M+1).

Example 7.b.

$R^1$=2-(1-naphthyl)ethyl: Using a procedure similar to that described in Example 4.b., except that sodium bicarbonate was not used and that water was used instead of 1N hydrochloric acid in the extractive work-up, the product of Example 7.a. was converted into material which was purified by trituration with methanol to afford the alcohol (0.130 g) as a solid; TLC: $R_f$=0.43, chloroform:methanol (95:5); MS: m/z=545(M+1).

Example 8.b.

$R^1$=2-phenylcyclopropyl: Using a procedure similar to that described in Example 4.b., except that sodium bicarbonate was not used and that water was used instead of 1N hydrochloric acid in the extractive work-up, the product of Example 8.a. was converted into material which was purified by trituration with methanol and ether to afford the alcohol (0.207 g) as a solid; TLC: $R_f$=0.17, chloroform:methanol (95:5); MS: m/z=507(M+1).

Example 9.b.

$R^1$=phenacyl: Using a procedure similar to that described in Example 4.b., except that sodium bicarbonate was not used and that water was used instead of 1N hydrochloric acid in the extractive work-up, the product of Example 7.a. was converted into material which was purified by crystallization from chloroform:methanol:ether to afford the alcohol (0.245 g) as a white solid; TLC: $R_f$=0.17, chloroform:methanol (95:5); MS: m/z=509(M+1).

Example 10.b.

$R^1$=α,α-dimethylphenethyl: Using a procedure similar to that described in Example 4.b., except that sodium bicarbonate was not used and that water was used instead of 1N hydrochloric acid in the extractive work-up, the product of Example 10.a. was converted into material which was purified by chromatography, eluting with hexanes:acetone (gradient, 4:1, 3:1, 2:1), to afford the alcohol (0.260 g) as a yellow foam; TLC: $R_f$=0.15, chloroform:methanol (97:3); MS: m/z=523(M+1).

Example 11.b.

R$^1$=tert-butoxycarbonylmethyl: Using a procedure similar to that described in Example 4.b., except that sodium bicarbonate was not used and that water was used instead of 1N hydrochloric acid in the extractive work-up, the product of Example 11.a. was converted into material that was purified by chromatography, eluting with hexanes:acetone (gradient, 2:1, 1:1), to afford the alcohol (0.210 g) as a solid; TLC: R$_f$=0.14, chloroform:methanol (97:3); MS: m/z=449 (M+1).

Example 12.b.

R$^1$=methoxycarbonylmethyl: Using a procedure similar to that described in Example 4.b., except that sodium bicarbonate was not used, that water was used instead of 1N hydrochloric acid in the extractive work-up, and that the combined aqueous washes were extracted with chloroform and the combined organic extracts dried and evaporated, the product of Example 12.a. was converted into material, which was purified by chromatography eluting with hexanes:acetone (gradient, 1:1, 1:2). The resulting material was triturated with ethanol:water to afford the alcohol (0.240 g) as a tan solid; TLC: R$_f$=0.08, chloroform:methanol (97:3); MS: m/z=463(M+1).

Example 13.b.

R$^1$=benzyloxycarbonylmethyl: Using a procedure similar to that described in Example 4.b., except that sodium bicarbonate was not used and that water was used instead of 1N hydrochloric acid in the extractive work-up, the product of Example 13.a. was converted into material which was purified by chromatography, eluting with a gradient of hexanes:acetone (gradient, 2:1, 1:1), to afford the alcohol (0.260 g) as an off-white solid; TLC: R$_f$=0.30, chloroform:methanol (95:5); MS: m/z=539(M+1).

EXAMPLE 14

2-[3-(2-Morpholinoethyl)-2,4,8-trioxo-1,2,3,4,7,8-hexahydropyrido-[3,4-d]pyrimidin-7-yl]-N-(3,3,3-trifluoro-1-isopropyl-2-oxopropyl)acetamide.

Using a procedure similar to that described in Example 1, except that no sodium bicarbonate wash was used, that saturated NH$_4$Cl was used instead of 1N hydrochloric acid in the extractive work-up, and that the combined aqueous washes were made basic (pH 8) with NaOH and extracted with chloroform and the combined chloroform layers were dried and evaporated, the product of Example 14.b. was converted into material that was purified by chromatography, eluting with chloroform:methanol:ammonium hydroxide (90:10:1). The resulting material was repurified by chromatography, eluting with hexanes:acetone (gradient, 1:1, 1:2, 1:3, 0:1). This material was again purified by chromatography, eluting with dichloromethane:methanol (gradient, 100:0, 99:1) to afford the title compound (0.40 g) as an orange oil; TLC: R$_f$=0.23, chloroform:methanol:NH$_4$OH (90:10:1); MS: m/z=502(M+1). Analysis for C$_{21}$H$_{26}$F$_3$N$_5$O$_6$.0.70 H$_2$O: Calculated: C, 49.07; H, 5.37; N, 13.62; Found: C, 49.17; H, 5.29; N, 13,40.

The intermediate alcohol used in Example 14 was prepared as follows:
a. 2-[3-(2-Morpholinoethyl)-2,4,8-trioxo-1,2,3,4,7,8-hexahyHropyrido-[3,4-d]pyrimidin-7-yl]-N-(2-tert-butyldimethylsilyloxy-3,3,3-trifluoro- 1-isopropylpropyl)acetamide.

A solution of the acid from Example 1.g. (0.500 g), 2-morpholinoethylamine (0.318 mL), and 1-hydroxybenzotriazole hydrate (0.220 g) in dimethylformamide (5 mL) was treated with 1-(3-dimethylaminopropyl)-3-ethylcarbodiimide hydrochloride (0.172 g) and stirred at room temperature for 16 hours. The mixture was diluted with ethyl acetate, washed (1N hydrochloric acid, 1N NaOH, brine), and the acidic washes were saturated with sodium chloride, made basic with saturated sodium bicarbonate, and extracted with chloroform. The combined chloroform and ethyl acetate layers were dried and evaporated. The residue was dissolved in dimethylformamide (5 mL), heated at 120° C. for 2 hours, taken up in chloroform, washed with brine, dried and evaporated to afford the bicyclic compound (0.400 g) as a brown oil that was used without further purification; TLC: R$_f$=0.43, methanol:chloroform (5:95); MS: m/z=618(M+1).
b. 2-[3-(2-Morpholinoethyl)-2,4,8-trioxo-1,2,3,4,7,8-hexahydropyrido-[3,4-d]pyrimidin-7-yl]-N-(3,3,3-trifluoro-2-hydroxy-1-isopropylpropyl)acetamide.

Using a procedure similar to that described in Example 4.b., except that neither the 1N hydrochloric acid nor sodium bicarbonate were used in the extractive work-up, the product of Example 14.a. was converted into material which was purified by chromatography, eluting with hexanes:acetone (gradient, 1:1, 1:2, 0:1), to afford the alcohol (0.240 g) as a tan foam; TLC: R$_f$=0.31, chloroform:methanol (95:5); MS: m/z=504(M+1).

EXAMPLE 15

[3-(4-Methoxybenzyl)-2,4,8-trioxo-1,2,3,4,7,8-hexahydropyrido-[3,4-d]pyrimidin-7-yl]-N-(3,3,3-trifluoro-1-isopropYl-2-oxopropyl)acetamide.

Using a procedure similar to that described in Example 1, except that ethyl acetate was used instead of chloroform in the extractive work-up, the product of Example 15.c. was converted into material which was purified by chromatography, eluting with chloroform:methanol (gradient, 100:0, 97.5:2.5), to afford the title compound (0.170 g) as a white solid; TLC: R$_f$=0.29, chloroform:methanol (95:5); HPLC, t$_R$=8.35, Col A, FR=2, water:acetonitrile (7:3) MS: m/z=509(M+1). Analysis for C$_{23}$H$_{23}$F$_3$N$_4$O$_6$: Calculated: C, 54.33; H, 4.56; N, 11.02; Found: C, 53.90; H, 4.60; N, 10.75.

The intermediate alcohol used in Example 15 was prepared as follows:
a. 2-[3-Benzyloxycarbonylamino-4-(4-methoxybenzylaminocarbonyl)- 2-oxo-1,2-dihydro-1-pyridyl]-N-(2-tert-butyldimethylsilyloxy-3,3,3-trifluoro- 1-isopropylpropyl)acetamide.

A solution of the acid from Example 1.g. (0.550 g), 4-methoxybenzylamine (0.234 mL), and 1-hydroxybenzotriazole hydrate (0.241 g) in dimethylformamide (5 mL) was treated with 1-(3-dimethylaminopropyl)-3-ethylcarbodiimide hydrochloride (0.189 g), stirred at room temperature for 16 hours, taken up in chloroform, washed (1N hydrochloric acid, 1N NaOH, brine), dried and evaporated. The product was purified by chromatography, eluting with acetone:hexanes (gradient, 25:75, 35:65), to afford the amide (0.566 g) as a solid; TLC: R$_f$=0.52, methanol:chloroform (5:95); MS: m/z=733(M+1).
b. 2-[3-(4-Methoxybenzyl)-2,4,8-trioxo-1,2,3,4,7,8-hexahydropyrido-[3,4-d]pyrimidin-7-yl]-N-(2-tert-butyldimethylsilyloxy-3,3,3-trifluoro- 1-isopropylpropyl)acetamide.

A solution of the product of Example 15.a. (0.550 g) in dimethylformamide (8 mL) was heated at 120° C. for 2 hours and evaporated. The material was purified by chromatography, eluting with acetone:hexanes (gradient, 20:80, 25:75, 30:70), to afford the bicyclic compound (0.469 g) as an off-white foam; TLC: $R_f$=0.49, acetone:hexanes (3:7); MS: m/z=625(M+1).

c. 2-[3-(4-Methoxybenzyl)-2,4,8-trioxo-1,2,3,4,7,8-hexahydropyrido-[3,4-d]pyrimidin-7-yl]-N-(3,3,3-trifluoro-2-hydroxy-1-isopropylpropyl)acetamide.

Using a procedure similar to that of Example 4.b., except that the reaction was run at room temperature instead of 0° C. the product of Example 15.b. (0.460 g) was converted into the alcohol (0.350 g) and used without further purification; TLC: $R_f$=0.23, acetone:hexanes (1:1); MS: m/z=511(M+1).

EXAMPLE 16

2-[3-(4-Methoxybenzyl)-2,4,8-trioxo-6-phenyl-1,2,3,4,7,8-hexahydro-pyrido-[3,4-d]pyrimidin-7-yl]-N-(3,3,3-trifluoro-1-isopropyl-2-oxopropyl)acetamide.

A solution of the alcohol from Example 16.h. (0.710 g) in dimethyl sulfoxide:toluene (1:1, 30 mL) was treated with 1-(3-dimethylamino-propyl)-3-ethylcarbodiimide hydrochloride (2.32 g), cooled to 0° C. and treated with 2,2-dichloroacetic acid (0.40 mL). The reaction mixture was stirred at room temperature for 16 hours and was partitioned between ethyl acetate and 1N hydrochloric acid. The organic layer was washed (1N hydrochloric acid, brine, saturated sodium bicarbonate, brine), dried and evaporated. The product was purified by chromatography, eluting with methanol:chloroform (gradient, 1:99, 3:97), to afford the title compound (0.38 g) as an off-white solid; TLC: $R_f$=0.38, methanol:chloroform (3:97); HPLC, $t_R$=4.31, Col A, FR=2, water:acetonitrile (1:1); MS: m/z=585(M+1). Analysis for $C_{29}H_{27}F_3N_4O_6 \cdot 0.80\ CH_3OH$: Calculated: C, 58.66; H, 4.99; N, 9.18; Found: C, 59.04; H, 5.38; N, 8.68.

The intermediate alcohol used in Example 16 was prepared as follows:

a. (α-Chlorobenzylidine)dimethylammonium chloride.

A solution of N,N-dimethylbenzamide (20.0 g) in dichloromethane (150 mL) was treated with oxalyl chloride (30.0 mL) and stirred at room temperature for 3 hours. The solution was evaporated, diluted with hexanes, stirred vigorously until a solid formed and the solvent was decanted. The residue was triturated with hexanes, then ether, and evaporated to afford a moisture sensitive white solid which was stored under vacuum and used without further purification.

b. Dimethyl (2-ethoxycarbonyl-3-dimethylamino-3-phenyl-2-propenylidene)malonate.

A suspension of hexanes washed sodium hydride (8.0 g, 60% oil dispersion) in tetrahydrofuran (300 mL) at 0° C. was treated with the product of Example 1.j. (40.0 g), stirred at room temperature for 4.5 hours, cooled to 0° C. and treated with a suspension of the product of Example 16.a in tetrahydrofuran (100 mL). The mixture was stirred at room temperature for 1 hour. The resulting material was filtered through silica gel (1000 mL), eluting with ether, until no yellow colored material appeared in the filtrate. The resulting ether solution was evaporated and the residue was triturated with ether and filtered to afford the diene (13.1 g) as yellow crystals. The filtrate was evaporated and the residue purified by chromatography, eluting with ether:hexanes (1:1). The fractions containing the product were combined and evaporated without external heat until additional product (8.5 g) crystallized; TLC: $R_f$=0.29, ether:hexanes (7:3); MS: m/z=362(M+1).

c. 2-(4-Ethoxycarbonyl-3-methoxycarbonyl-2-oxo-6-phenyl-1,2-dihydro-1-pyridyl)-N-(2-tert-butyldimethylsilyloxy-3,3,3-trifluoro-1-isopropylpropyl)acetamide.

A mixture of the product from Example 16.b (18.0 g) and the amine from Example 1.c. (18.0 g) was heated under vacuum (133 Pa) at 120° C. for 8 hours, treated with additional amine (6.0 g), heated under vacuum at 120° C. for 16 hours and cooled to room temperature. The residue was taken up in ether, washed (1N hydrochloric acid, 1N NaOH, brine) dried ($K_2CO_3$: $Na_2SO_4$, 1:1) and evaporated. The material was purified by chromatography, eluting with ether:hexanes (gradient, 40:60, 50:50, 55:45, 60:40, 70:30, 100:0). The impure fractions were purified by chromatography, eluting with ether:hexanes (gradient, 50:50, 55:45, 60:40, 70:30, 80:20, 100:0) and the resulting material was combined with the pure material from the first column to afford the product (14.9 g) as a solid; TLC: $R_f$=0.41, acetone:hexanes (3:7); MS: m/z=627(M+1).

d. 2-(3-Carboxy-4-ethoxycarbonyl-2-oxo-6-phenyl-1,2-dihydro-1-pyridyl)-N-(2-tert-butyldimethylsilyloxy-3,3,3-trifluoro-1-isopropylpropyl)acetamide.

A solution of the product of Example 16.c. (14.9 g) and anhydrous LiI (7.49 g) in pyridine (250 mL) was heated at reflux for 4 hours, diluted with ether, washed (1N hydrochloric acid, brine), dried and evaporated. The residue was taken up in ether, was washed (6N hydrochloric acid, 1N hydrochloric acid, brine), dried and evaporated. The product was purified by chromatography, eluting with methanol:chloroform (gradient, 0:100, 5:95, 10:90, 15:85, 20:80, 30:70, 50:50), to afford the acid (13.1 g) as a gray foam; TLC: $R_f$=0.56, methanol:chloroform:acetic acid (5:95:1); MS: m/z=631(M+1).

e. 2-(3-Benzyloxycarbonylamino-4-ethoxycarbonyl-2-oxo-6-phenyl-1,2-dihydro-1-pyridyl)-N-(2-tert-butyldimethylsilyloxy-3,3,3-trifluoro-1isopropylpropyl)acetamide.

A solution of the acid of Example 16.d. (31.1 g), diphenylphosphoryl azide (6.91 mL), triethylamine (4.74 mL) and benzyl alcohol (3.77 mL) in p-dioxane (200 mL) was heated at reflux for 4 hours and evaporated. The residue was taken up in ether, and was washed (1N hydrochloric acid, brine, 1N NaOH, brine), dried ($K_2CO_3$: $Na_2SO_4$, 1:1) and evaporated. The material was purified by chromatography, eluting with ethyl acetate:hexanes (15:85), to afford the product (12.8 g) as a tan semisolid; TLC: 0.36, ethyl acetate:hexanes (3:7); MS: m/z=718(M+1).

f. 2-(3-Benzyloxycarbonylamino-4-carboxy-2-oxo-6-phenyl-1,2-dihydro-1-pyridyl)-N-(2-tert-butyldimethylsilyloxy-3,3,3-trifluoro-1-isopropylpropyl)acetamide.

A solution of the product of Example 16.e. (11.0 g) in ethanol:water (270 mL, 100:35) at 0° C. was treated with $LiOH \cdot H_2O$ (0.674 g), stirred for 4 hours, treated with additional $LiOH \cdot H_2O$ (0.674 g), diluted with ether, washed (1N hydrochloric acid, brine), dried and evaporated. The product was purified by chromatography, eluting with methanol:chloroform:acetic acid (gradient, 0:100:0, 2.5:97.5:0, 5:95:0, 5:95:1), to afford the acid (5.6 g) as an off-white foam; TLC: $R_f$=0.30, methanol:chloroform (1:9); MS: m/z=690(M+1).

g. 2-[3-(4-Methoxybenzyl)-2,4,8-trioxo-6-phenyl-1,2,3,4,7,8-hexahydropyrido-[3,4-d]pyrimidin-7-yl]-N-(2-tert-butyldimethylsilyloxy-3,3,3-trifluoro-1-isopropylpropyl)acetamide.

A solution of the acid of Example 16.f. (1.50 g), 4-methoxybenzylamine (0.57 mL), and 1-hydroxybenzotriazole hydrate (0.588 g) in dimethylformamide (15 mL) was treated with 1-(3-dimethylaminopropyl)-3-ethylcarbodiimide hydrochloride (0.501 g) and stirred at room temperature for 16 hours. The mixture was dissolved in ethyl acetate, washed (1N hydrochloric acid, brine, saturated sodium bicarbonate, brine), dried and evaporated. The residue was dissolved in dimethylformamide (15 mL), heated at 120° C. for 2.5 hours, taken up in ethyl acetate, washed (1N hydrochloric acid, brine, saturated sodium bicarbonate, brine), dried and evaporated. The product was purified by chromatography, eluting with hexanes:acetone (8:2), to afford the bicyclic compound (0.940 g) as a light yellow foam; TLC: $R_f$=0.35, hexanes:acetone (8:2); MS: m/z=701(M+1).

h. 2-[3-(4-Methoxybenzyl-2,4,8-trioxo-6-phenyl-1,2,3,4,7, 8-hexahydropyrido-[3,4-d]pyrimidin-7-yl]-N-(3,3,3-trifluoro-2-hydroxy-1isopropylpropyl)acetamide.

A solution of the product of Example 16.g (0.920 g) in tetrahydrofuran (15 mL) was treated with tetrabutylammonium fluoride (1.58 mL, 1.0M in THF), stirred at room temperature for 2 hours and evaporated. The material was purified by chromatography, eluting with chloroform:methanol (gradient, 97:3, 95:5), to afford the product (0.730 g) as an off-white solid; TLC: $R_f$=0.20, methanol:chloroform (5:95); MS: m/z=587(M+1).

EXAMPLE 17

2-(3-Methyl-2,4,8-trioxo-6-phenyl-1,2,3,4,7,8-hexahydropyrido[3,4-d]-pyrimidin- 7-yl)-N-(3,3,3-trifluoro-1-isopropyl-2-oxopropyl)acetamide.

Using a procedure similar to that described in Example 16, except using 1N hydrochloric acid:brine (1:1) instead of 1N hydrochloric acid:saturated sodium bicarbonate:brine for the washings, the product of Example 17.b. was converted into material which was purified by chromatography, eluting with methanol:chloroform (2:98), to afford the title product (0.197 g) as a white solid; TLC: $R_f$=0.40, methanol:chloroform (5:95); HPLC, $t_R$=4.76, Col A, FR=2, water:acetonitrile (65:35); MS: m/z=479(M+1), 310. Analysis for $C_{22}H_{21}F_3N_4O_5 \cdot 1.2 H_2O$: Calculated: C, 52.84; H, 4.71; N, 11.20; Found: C, 52.81; H, 4.72; N, 10.79.

The intermediate alcohol used in Example 17 was prepared as follows:

a. 2-(3-Methyl-2,4,8-trioxo-6-phenyl-1,2,3,4,7,8-hexahydropyrido-[3,4-d]pyrimidin-7-yl)-N-(2-tert-butyldimethylsilyloxy-3,3,3-trifluoro- 1-isopropylpropyl)acetamide.

Using a procedure similar to that described in Example 16.g., except using methylamine hydrochloride (4 equivalents) instead of 4-methoxybenzylamine, and using 4-methylmorpholine (5 equivalents) as an acid scavenger, the product of Example 16.f. was converted into the bicyclic compound (0.610 g) and used without purification; TLC: $R_f$=0.54, hexanes:acetone (4:6); MS: m/z=595(M+1).

b. 2-(3-Methyl-2,4,8-trioxo-6-phenyl-1,2,3,4,7,8-hexahydropyrido-[3,4-d]pyrimidin-7-yl)-N-(3,3,3-trifluoro-2-hydroxy-1-isopropylpropyl)acetamide.

Using a procedure similar to that described in Example 16.h., the product of Example 17.a. was converted to material that was purified by chromatography, eluting with methanol:chloroform (5:95), to afford the alcohol (0.330 g) as a vhite solid; TLC: $R_f$=0.29, methanol chloroform (5:95); MS: m/z=481(M+1). Analysis for $C_{22}H_{23}F_3N_4O_5 \cdot 1.6 H_2O$: Calculated: C, 51.88; H, 5.18; N, 11.00; Found: C, 51.79; H, 4.96; N, 10.81.

EXAMPLE 18

2-[3-(α,α-Dimethylphenethyl)-2,4,8-trioxo-6-phenyl-1,2,3, 4,7,8-hexahydropyrido-[3,4-d]pyrimidin-7-yl)-N-(3,3,3-trifluoro-1-isopropyl-2oxopropyl)acetamide.

Using a procedure similar to that described in Example 16, the product of Example 18.b. was converted into material which was purified by chromatography, eluting with methanol:chloroform (1:99), to afford the title product (0.215 g) as a yellow solid; TLC: $R_f$=0.42, methanol:chloroform (2.5:97.5); HPLC, $t_R$=6.09, Col A, FR=3, water:acetonitrile (1:1); MS: m/z=597(M+1). Analysis for $C_{31}H_{31}F_3N_4O_5 \cdot 0.5 H_2O$: Calculated: C, 61.48; H, 5.32; N, 9.25; Found: C, 61.35; H, 5.34; N, 8.98.

The intermediate alcohol used in Example 18 was prepared as follows:

a. 2-[3-(α,α-Dimethylphenethyl)-2,4,8-trioxo-6-phenyl-1,2, 3,4,7,8-hexahydropyrido-[3,4-d]pyrimidin-7-yl)-N-(2-tert-butyldimethylsilyloxy- 3,3,3-trifluoro-1-isopropylpropyl)acetamide.

Using a procedure similar to that described in Example 16.g., except using α,α-dimethylphenethylamine instead of 4-methoxybenzylamine, the product of Example 16.f. was converted into material that was purified by chromatography, eluting with ether:hexanes (gradient, 70:30, 80:20), to afford the bicyclic compound (0.520 g) as a yellow oil; TLC: $R_f$=0.51, methanol:chloroform (2.5:97.5); MS: m/z=713(M+ 1).

Lower $R_f$ material (0.210 g) was also collected and determined to be the same material as the product from Example 18.b.

b. 2-[3-(α,α-Dimethylphenethyl)-2,4,8-trioxo-6-phenyl-1,2, 3,4,7,8-hexahydropyrido-[3,4-d]pyrimidin-7-yl)-N-(3,3,3-trifluoro-2-hydroxy-1-isopropylpropyl)acetamide.

Using a procedure similar to that described in Example 16.h., except that the initially isolated product was washed (1N hydrochloric acid, brine, saturated sodium bicarbonate), dried and evaporated, the product of Example 18.a. was converted into material which was combined with the lower $R_f$ material from Example 18.a. and purified by chromatography, eluting with acetone:hexanes (35:65), to afford the alcohol (0.295 g) as a light tan solid; TLC: $R_f$=0.33, methanol chloroform (2.5:97.5); MS: m/z=599(M+1).

EXAMPLE 19

2-(3-Acetonyl-2,4,8-trioxo-1,2,3,4,7,8-hexahydropyrido[3, 4-d]-pyrimidin- 7-yl)-N-(3,3,3-trifluoro-1-isopropyl-2-oxopropyl)acetamide.

Using a procedure similar to that described in Example 1, except that a second equivalent of carbodiimide and dichloroacetic acid vas added after 16 hours and the mixture stirred an additional 24 hours, and no sodium bicarbonate wash was used in the extractive work-up, the product of Example 19.b. was converted into material which was purified by chromatography, eluting vith chloroform:methanol (gradient, 99:1, 98:2, 95:5). The resulting material was repurified by chromatography, eluting with chloroform:methanol (gradient, 99:1, 98:2), to afford the title compound (0.086 g) as a white solid; TLC: $R_f$=0.74, chloroform:methanol (85:15); MS: m/z=445(M+1). Analysis for $C_{18}H_{19}F_3N_4O_6 \cdot 0.2 C_6H_{14} \cdot 0.6 H_2O$: Calculated: C, 48.82; H, 4.91; N, 11.86; Found: C, 48.80; H, 4.78; N, 11.74.

The intermediate alcohol used in Example 19 was prepared as follows:

a. 2-[Benzyloxycarbonylamino-4-(2-hydroxypropylaminocarbonyl)-2-oxo-1,2-dihydro-1-pyridyl]-N-(2-tert-butyldimethylsilyloxy-3,3,3-trifluoro- 1-isopropylpropyl)acetamide.

Using a procedure similar to that described in Example 15.a., except that 2-hydroxypropylamine was used instead of 4-methoxybenzylamine, the product of Example 1.g. was converted into the amide (0.480 g), which was used without further purification; TLC: $R_f$=0.21, chloroform:methanol (95:5); MS: m/z=563(M+1).

b. 2-[3-(2-Hydroxypropyl)-2,4,8-trioxo-1,2,3,4,7,8-hexahydropyrido-[3,4-d]pyrimidin-7-yl]-N-(3,3,3-trifluoro-2-hydroxy-1-isopropylpropyl)acetamide.

A solution of the product of Example 19.a. (0.450 g) in dimethylformamide (5 mL) was heated at 120° C. for 3 hours, cooled to 0° C., treated with tetrabutylammonium fluoride (1.1 mL, 1.0M in THF), stirred at 0° C. for 0.5 hours, partitioned between brine and chloroform, washed (brine), dried and evaporated. The material was purified by chromatography, eluting with chloroform:methanol (9:1), and repurified by chromatography, eluting with chloroform:methanol:ammonium hydroxide (85:15:1), to afford the alcohol (0.480 g) as an orange foam; TLC: $R_f$=0.12, chloroform:methanol (9:1); MS: m/z=449(M+1).

EXAMPLES 20–28

Using a synthetic sequence similar to that outlined in Scheme II the following compounds of formula I wherein $R^1$ and $R^2$ have the indicated values were prepared.

Example 20

$R^1$=benzyloxycarbonyl; $R^2$=phenyl: Analysis for $C_{30}H_{27}F_3N_4O_7 \cdot 0.6\ H_2O$: Calculated: C, 57.80; H, 4.56; N, 8.98; Found: C, 57.81; H, 4.54; N, 8.50.

Example 21

$R^1$=N-methylcarbamoylmethyl; $R^2$=phenyl: Analysis for $C_{24}H_{24}N_5O_6F_3 \cdot 1.0\ H_2O$: Calculated: C, 51.74; H, 4.78; N, 12.57; Found: C, 52.75; H, 4.84; N, 11.44.

Example 22

$R^1$=N-benzylcarbamoylmethyl; $R^2$=phenyl: Analysis for $C_{20}H_{28}N_6F_3 \cdot 2.0\ H_2O$: Calculated: C, 55.64; H, 4.98; N, 10.81; Found: C, 55.74; H, 5.07; N, 10/04.

Example 23

$R^1$=hydrogen; $R^2$=phenyl: Analysis for $C_{21}H_{19}N_4O_5F_3 \cdot 1.1\ H_2O$: Calculated: C, 52.09; H, 4.41; N, 11.57; Found: C, 52.01; H, 4.55; N, 11.01.

Example 24

$R^1$=2-ethoxyethyl; $R^2$=phenyl: Analysis for $C_{25}H_{27}N_4O_6F_3 \cdot 1.0\ H_2O$: Calculated: C, 54.15; H, 5.27; N, 10.10; Found: C, 54.04; H, 5.34; N, 9.69.

Example 25

$R^1$=carboxymethyl; $R^2$=hydrogen: Analysis for $C_{17}H_{17}N_4O_7F_3 \cdot 1.7\ H_2O$: Calculated: C, 42.82; H, 4.31; N, 11.75; Found: C, 42.91; H, 4.04; N, 11.18.

Example 26

$R^1$=dimethylamino; $R^2$-phenyl: TLC Rf 0.49 10% methanol:$CHCl_3$.

Example 27

$R^1$=morpholinomethyl; $R^2$=phenyl: TLC Rf 0.34 10% methanol:$CHCl_3$.

Example 28

$R^1$=carbamoylmethyl; $R^2$=phenyl: Analysis for $C_{23}H_{22}N_5OF_2 \cdot 2.5\ H_2O$: Calculated: C, 48.77; H, 4.80; N, 12.36; Found: C, 48.75; H, 4.70; N, 12.01.

FORMULAE

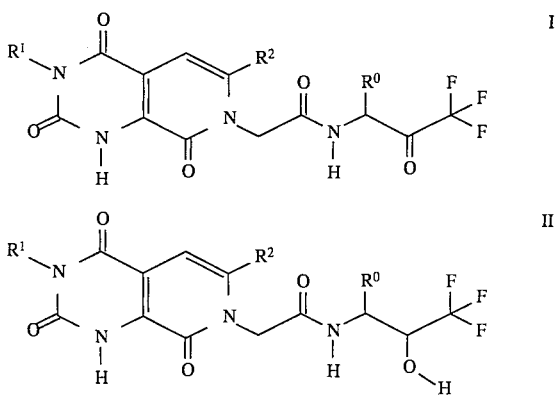

SCHEME I

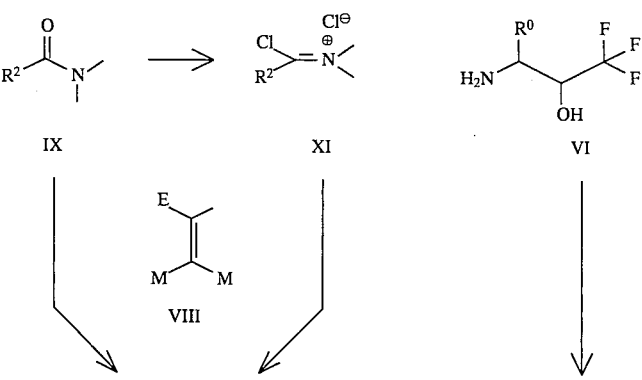

5,532,366

-continued
SCHEME I

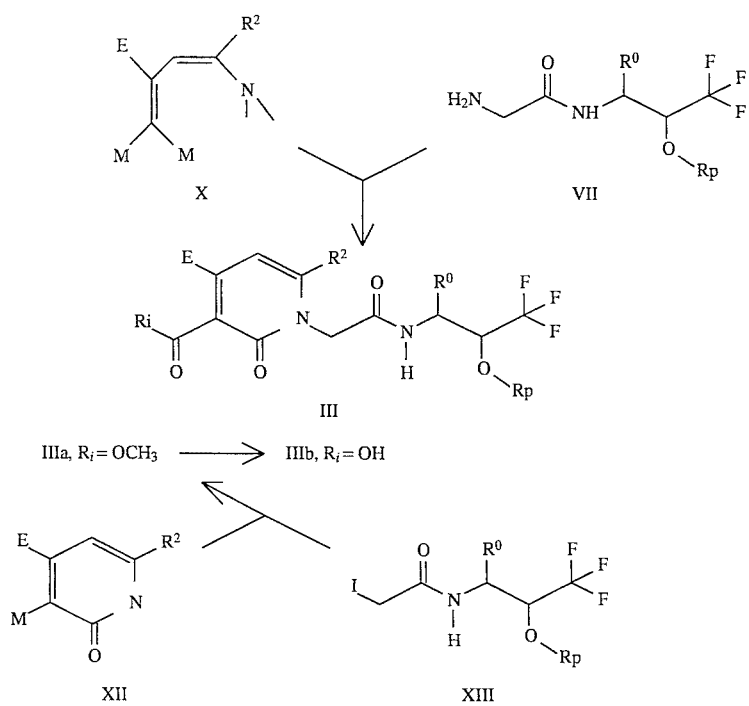

SCHEME II

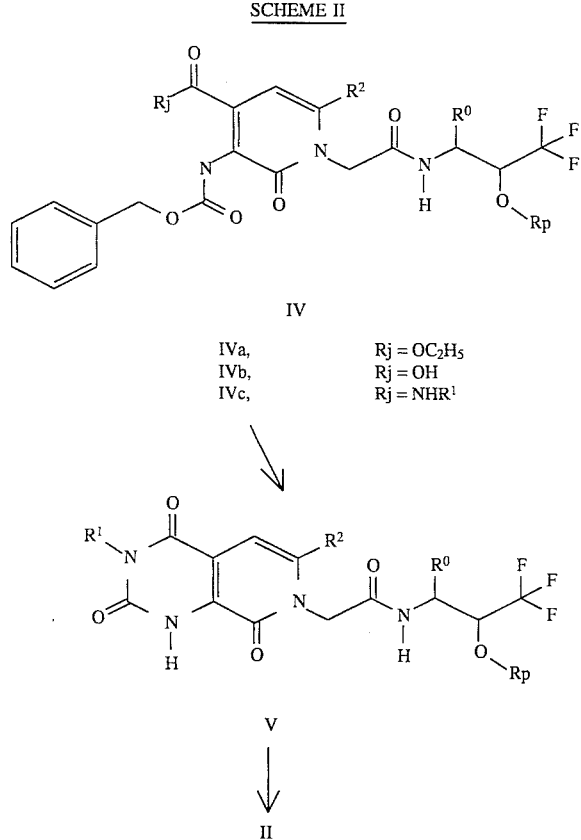

What is claimed is:

1. A compound of formula I:

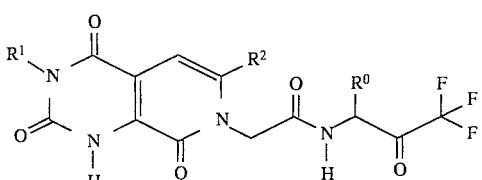

wherein:

$R^0$ is (1–5C) alkyl;

$R^1$ is hydrogen, NReRf; or $R^1$ is (1–6C)alkyl, (3–6C)cycloalkyl, phenacyl, aryl, acetonyl or heteroaryl (or, where applicable, an N-oxide thereof,) any of which may bear one or more substituents selected from a group consisting of hydroxy, (1–6C)alkyl, (1–4C) alkoxy, (1–4C) acyloxy, COORa, CONRbRc, COO(CH$_2$)$_2$NReRf, cyano, SO$_2$R$^5$, CONRdSO$_2$R$^5$, NReRf, NRgCOR$^6$, NRgCOOR6, NRhCONRiRj, NRkSO$_2$R$^3$, SO$_2$NRlRm, SO$_2$NRnCOR$^4$, P(O) (ORa)$_2$, aryl and heteroaryl (or, where applicable, an N-oxide thereof,); and wherein an aryl or heteroaryl moiety of R$^1$ or a substituent thereof may bear one or more halogeno, nitro, (1–4C)alkyl, (1–4C) alkoxy or trifluoromethyl groups; wherein Ra—Rn are independently hydrogen, benzyl or (1–4C) alkyl; or, independently, a group NRbRc, NReRf, NRiRj or NRlRm is a cyclic radical selected from a group consisting of 1-pyrrolidinyl, piperidino, morpholino or 1-piperazinyl which may bear a (1–4C)alkyl or a halogeno substituent at the 4-position; or, independently, a group NReRf is a cyclic radical selected from a group consisting of 2-pyrrolidinon-1-yl, succinimido, oxazolidin-2-on-3-yl, 2-benzoxazolinon-3-yl, phthalimido and cis-hexahydrophthalimido; and $R^3$–$R^6$ are independently trifluoromethyl, (1–6C)alkyl, (3–6C)cycloalkyl, aryl or heteroaryl (or, where applicable, an N-oxide thereof,) in which the aryl or heteroaryl may bear one or more substituents selected from a group consisting of (1–4C)alkyl, hydroxy, (1–4C)alkoxy, halogeno or trifluoromethyl;

$R^2$ is hydrogen, (1–6C)alkyl, (3–6C)cycloalkyl or a radical of formula BY- in which B is aryl or heteroaryl (or, where applicable, an N-oxide thereof,) and may bear an aryl, or heteroaryl substituent and in which B or an aryl or heteroaryl substituent on B may independently bear one or more substituents selected from the group consisting of halogeno, nitro, (1–6C)alkyl, (3–6C)cycloalkyl, trifluoromethyl, cyano, hydroxy, (1–4C)alkoxy, acetoxy, $SO_2Ro$, $COORq$, $CONRrRs$; wherein Rq—Rs are independently hydrogen or (1–4C)alkyl;

Ro is (1–4C)alkyl; and

Y is a direct bond, methylene, ethylene, or trans-vinylene; and provided that no aliphatic carbon is bonded to more than one nitrogen or oxygen, except as part of a cyclic ketal, or as part of an ester qroup, or where the nitrogen bears a carbonyl group; or for a compound of formula I which is acidic or basic, a pharmaceutically acceptable salt thereof.

2. A compound as claimed in claim 1 wherein $R^1$ is hydrogen; or $R^1$ is (1–6C)alkyl, (3–6C)cycloalkyl, phenacyl, aryl or heteroaryl (or, where applicable, an N-oxide thereof,) any of which may bear one or more substituents selected from a group consisting of hydroxy, (1–4C)alkyl, (1–4C)alkoxy, (1–4C)acyloxy, COORa, CONRbRc, $COO(CH_2)_2NReRf$, cyano, $SO_2R^5$, $CONRdSO_2R^5$, NReRf, $NRgCOR^6$, $NRgCOOR^6$, NRhCONRiRj, $NRkSO_2R^3$, $SO_2NRlRm$, $SO_2NRnCOR^4$, $P(O)(ORa)_2$, aryl and heteroaryl (or, where applicable, an N-oxide thereof,) and wherein an aryl or heteroaryl moiety of $R^1$ or a substituent thereof may bear one or more halogeno, nitro, (1–4C)alkyl, )$_{1-4}$C)alkoxy or trifluoromethyl groups; and Ra-Rn are defined as in claim 1.

3. A compound as claimed in claim 1 or 2 wherein Ro is ethyl or isopropyl; (1–4C)alkyl is methyl, ethyl, propyl, isopropyl, butyl, isobutyl, or tert-butyl; (1–6C)alkyl is methyl, ethyl, propyl, isopropyl, butyl, isobutyl, tert-butyl, pentyl, 3-methylbutyl, nl-ethylpropyl, hexyl or 4-methylpentyl; (3–6C)cycloalkyl is cyclopropyl, cyclopentyl or cyclohexyl; aryl is phenyl, indenyl, napthyl; aryl substituted with halOqenO is 4-halophenyl; heteroaryl is furyl, imidazolyl, tetrazolyl, pyridyl (or its N-oxide), thienyl, pyrimidinyl (or its N-oxide), indolyl or quinolinyl (or its N-oxide); lower acyloxy is acetoxy; (1–4C)alkoxy is methoxy, ethoxy, propoxy, isopropoxy or t-butoxy; halogeno is bromo, chloro or fluoro; Ra, Rd Rg, Rh, Rk and Rn independently is hydrogen, methyl, ethyl, isopropyl; NRbRc, NReRf, NRiRj or NRlRm is independently morpholino, 1-pyrloidinyl, piperidino or 1-piperazinyl; $R^3$–$R^6$ independently is methyl, ethyl, isopropyl or phenyl; $R^1$ is 1-napthylmethyl, 2-(1-napthyl)ethyl, phenethyl, α,α-dimethylphenethyl, methyl, benzyloxycarbonylmethyl or 4-methoxybenzyl; and $R^2$ is hydrogen or phenyl.

4. A compound as claimed in claim 3 wherein $R^0$ is isopropyl; and $R^1$ is 1-naphthylmethyl, 2-(1-naphthyl)ethyl, α,α-dimethylphenethyl, or benzyloxycarbonylmethyl.

5. A compound as claimed in claim 1 wherein $R^1$ is 1-naphthylmethyl, 2-(1-naphthyl)ethyl, α,α-dimethylphenethyl or benzyloxycarbonylmethyl; and $R^2$ is hydrogen.

6. A compound as claimed in claim 1 wherein $R^1$ is 1-naphthylmethyl, 2-(1-naphthyl)ethyl, α,α-dimethylphenethyl or benzyloxycarbonylmethyl; and $R^2$ is phenyl in which the phenyl may bear one or two halogeno, trifluoromethyl, methyl, hydroxy, methoxy, tert-butoxy, methoxycarbonyl or carboxy substituents.

7. A compound as claimed in claim 6 wherein $R^2$ is phenyl.

8. A salt as claimed in claim 1 selected from (a) for an acidic compound of formula I, an alkalai metal salt, an alkaline earth metal salt, an aluminum salt, an ammonium salt, or a salt made from an organic base; and (b) for a basic compound of formula I, an acid-addition salt made with an acid which provides a pharmaceutically acceptable anion.

9. A compound of formula II:

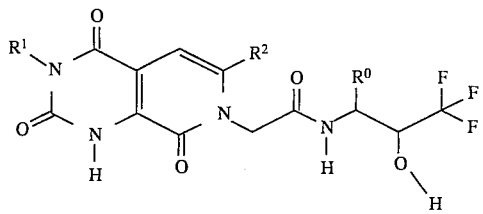

wherein $R^0$ is (1–5C)alkyl;

$R^1$ is hydrogen, NReRf; or $R^1$ is (1–6C)alkyl, (3–6C)cycloalkyl, phenacyl, aryl, acetonyl or heteroaryl (or, where applicable, an N-oxide thereof,) any of which may bear one or more substituents selected from a group consisting of hydroxy, (1–4C)alkyl, (1–4C)alkoxy, (1–4C)acyloxy, COORa, CONRbRc, $COO(CH_2)_2NReRf$, cyano, $SO_2R^5$, $CONRdSO_2R^5$, NReRf, $NRgCOR^6$, $NRgCOOR^6$, NRhCONRiRj, $NRkSO_2R^3$, $SO_2NRlRm$, $SO_2NRnCOR^4$, $P(O)(ORa)_2$, aryl and heteroaryl (or, where applicable, an N-oxide thereof,); and wherein an aryl or heteroaryl moiety of $R^1$ or a substituent thereof may bear one or more halogeno, nitro, (1–4C)alkyl, (1–4C)alkoxy or trifluoromethyl groups; wherein Ra—Rn are independently hydrogen, benzyl or (1–4C)alkyl; or, independently, a group NRbRc, NReRf, NRiRj or NRlRm is a cyclic radical selected from a group consisting of 1-pyrrolidinyl, piperidino, morpholino or 1-piperazinyl which may bear a (1–4C)alkyl or a halogeno substituent at the 4-position; or, independently, a group NReRf is a cyclic radical selected from a group consisting of 2-pyrrolidinon-1-yl, succinimido, oxazolidin-2-on-3-yl, 2-benzoxazolinon-3-yl, phthalimido and cis-hexahydrophthalimido; and $R^3$–$R^6$ are independently trifluoromethyl, (1–6C)alkyl, (3–6C)cycloalkyl, aryl or heteroaryl (or, where applicable, an N-oxide thereof,) in which the aryl or heteroaryl may bear one or more substituents selected from a group consisting of (1–4C)alkyl, hydroxy, (1–4C)alkoxy, halogeno or trifluoromethyl;

$R^2$ is hydrogen, (1–6C)alkyl, (3–6C)cycloalkyl or a radical of formula B.Y- in which B is aryl or heteroaryl (or, where applicable, an N-oxide thereof,) and may bear an aryl, or heteroaryl substituent and in which B or an aryl or heteroaryl substituent on B may independently bear one or more substituents selected from the group consisting of halogeno, nitro, (1–6C)alkyl, (3–6C)cycloalkyl, trifluoromethyl, cyano, hydroxy, (1–4C)alkoxy, acetoxy, $SO_2Ro$, $COORq$, $CONRrRs$; wherein Rq—Rs are independently hydrogen or (1–4C)alkyl;

Ro is (1–4C)alkyl; and

Y is a direct bond, methylene, ethylene, or trans-vinylene; and provided that no aliphatic carbon is bonded to more than one nitrogen or oxygen, except as part of a cyclic ketal, or as part of an ester qroup, or where the nitrogen bears a carbonyl group; or for a compound of formula II which is acidic or basic, a pharmaceutically acceptable salt thereof.

10. A pharmaceutical composition comprising a compound as defined in claim 1, or a pharmaceutically acceptable salt thereof, and a pharmaceutically acceptable diluent or carrier.

11. A method of treating emphysema comprising administering to a patient in need of treatment thereof a pharmaceutically effective amount of a compound according to claim 1 or a pharmaceutically acceptable salt thereof.

* * * * *